(12) United States Patent
Bonutti et al.

(10) Patent No.: US 12,290,282 B2
(45) Date of Patent: *May 6, 2025

(54) EXPANDABLE ACCESS SYSTEMS AND METHODS

(71) Applicant: P Tech, LLC, Manalapan, FL (US)

(72) Inventors: Peter M. Bonutti, Manalapan, FL (US); Matthew M. Cremens, Effingham, IL (US)

(73) Assignee: P TECH, LLC, Manalapan, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/452,063

(22) Filed: Aug. 18, 2023

(65) Prior Publication Data
US 2024/0058035 A1 Feb. 22, 2024

Related U.S. Application Data

(63) Continuation of application No. 16/929,038, filed on Jul. 14, 2020, now Pat. No. 11,832,846, which is a continuation of application No. 15/297,227, filed on Oct. 19, 2016, now Pat. No. 10,709,474, which is a continuation of application No. 13/683,847, filed on Nov. 21, 2012, now Pat. No. 9,498,249.

(51) Int. Cl.
*A61B 17/34* (2006.01)
*A61M 25/00* (2006.01)
*A61M 25/06* (2006.01)

(52) U.S. Cl.
CPC ...... *A61B 17/3439* (2013.01); *A61B 17/3498* (2013.01); *A61M 25/0662* (2013.01); *A61B 2017/3441* (2013.01); *A61B 17/3462* (2013.01); *A61M 2025/0024* (2013.01)

(58) Field of Classification Search
CPC ............ A61B 17/3439; A61B 17/3498; A61B 17/3462; A61B 2017/3441; A61M 25/0662; A61M 2025/0024
See application file for complete search history.

(56) References Cited

U.S. PATENT DOCUMENTS

| | | |
|---|---|---|
| 2,899,959 A | 2/1958 | Ginsburg |
| 3,598,118 A | 8/1971 | Warren |
| 3,788,318 A | 1/1974 | Kim et al. |
| 4,327,709 A | 5/1982 | Hanson et al. |
| 4,518,383 A | 5/1985 | Evans |

(Continued)

FOREIGN PATENT DOCUMENTS

WO 2008092782 8/2008

*Primary Examiner* — Theodore J Stigell
(74) *Attorney, Agent, or Firm* — Stinson LLP

(57) ABSTRACT

Embodiments may include an expandable access system having contracted and expanded configurations. The system and methods may include an expandable access device having a helix or wrapped shape. Embodiments may include a cannula, stent, needle, trocar, introducer, fastener, and/or any other devices disclosed herein. Embodiments may also include an expandable trocar positionable in at least a portion of the access device. A sleeve or band may be disposed over at least a portion of the access device and configured to resist radial expansion of the access device. Expansion of the trocar and/or receipt of an object may radially expand the access device between a contracted configuration and an expanded configuration.

20 Claims, 31 Drawing Sheets

(56) References Cited

U.S. PATENT DOCUMENTS

| | | | |
|---|---|---|---|
| 4,610,671 A | 9/1986 | Luther | |
| 4,716,901 A * | 1/1988 | Jackson | A61B 17/3439 |
| | | | 606/198 |
| 5,037,427 A | 8/1991 | Harada et al. | |
| 5,139,511 A | 8/1992 | Gill et al. | |
| 5,158,545 A | 10/1992 | Trudell et al. | |
| 5,158,548 A | 10/1992 | Lau et al. | |
| 5,183,464 A | 2/1993 | Dubrul et al. | |
| 5,257,975 A | 11/1993 | Foshee | |
| 5,314,418 A | 5/1994 | Takano et al. | |
| 5,431,676 A | 7/1995 | Dubrul et al. | |
| 5,707,359 A | 1/1998 | Bufallni | |
| 5,980,530 A | 11/1999 | Wilard | |
| 6,019,778 A | 2/2000 | Wilson et al. | |
| 6,162,236 A | 12/2000 | Osada | |
| 6,190,357 B1 | 2/2001 | Ferrari et al. | |
| 6,197,014 B1 | 3/2001 | Samson | |
| 6,280,412 B1 | 8/2001 | Pederson, Jr. | |
| 6,331,186 B1 | 12/2001 | Wang | |
| 6,595,946 B1 | 7/2003 | Pasqualucci | |
| 6,607,552 B1 | 8/2003 | Hanson | |
| 6,673,042 B1 | 1/2004 | Samson et al. | |
| 7,052,483 B2 | 5/2006 | Wojcik | |
| 7,144,388 B2 | 12/2006 | Crawford | |
| 7,306,617 B2 | 12/2007 | Majercak | |
| 7,449,011 B2 * | 11/2008 | Wenchell | A61B 17/3439 |
| | | | 606/198 |
| 7,597,688 B1 | 10/2009 | Masson | |
| 7,637,901 B2 | 12/2009 | Lawrence et al. | |
| 7,799,046 B2 | 9/2010 | White et al. | |
| 7,824,392 B2 | 11/2010 | Zhou | |
| 7,850,600 B1 * | 12/2010 | Piskun | A61B 17/0218 |
| | | | 604/164.11 |
| 7,883,474 B1 | 2/2011 | Mirigian et al. | |
| 7,896,897 B2 | 3/2011 | Gresham et al. | |
| 7,955,313 B2 | 6/2011 | Boismier | |
| 7,967,776 B2 | 6/2011 | Von Segesser | |
| 8,007,529 B2 | 8/2011 | Yan | |
| 8,070,731 B2 | 12/2011 | Wenchell et al. | |
| 8,105,288 B2 | 1/2012 | Keyser et al. | |
| 9,498,249 B2 * | 11/2016 | Bonutti | A61B 17/3439 |
| 10,709,474 B2 * | 7/2020 | Bonutti | A61M 25/0662 |
| 2002/0038141 A1 | 3/2002 | Yang | |
| 2003/0033000 A1 | 2/2003 | DiCaprio | |
| 2003/0171716 A1 | 9/2003 | Ejlersen | |
| 2004/0193113 A1 * | 9/2004 | Gillis | A61B 17/3468 |
| | | | 604/164.01 |
| 2004/0215307 A1 | 10/2004 | Mlichels et al. | |
| 2004/0236412 A1 | 11/2004 | Brar et al. | |
| 2005/0038408 A1 | 2/2005 | Von Segesser | |
| 2005/0070851 A1 | 3/2005 | Thompson | |
| 2005/0107817 A1 | 5/2005 | White | |
| 2005/0113901 A1 | 5/2005 | Coe | |
| 2006/0030922 A1 | 2/2006 | Dolan | |
| 2006/0036214 A1 | 2/2006 | Mogensen et al. | |
| 2006/0106415 A1 * | 5/2006 | Gabbay | A61B 17/3468 |
| | | | 606/198 |
| 2006/0201512 A1 | 9/2006 | Garrett et al. | |
| 2007/0233041 A1 | 10/2007 | Gellman | |
| 2008/0039917 A1 | 2/2008 | Cross et al. | |
| 2008/0243162 A1 | 10/2008 | Shibata et al. | |
| 2008/0287971 A1 | 11/2008 | Kuntz | |
| 2009/0259143 A1 | 10/2009 | Bakhtyari-Nejad-Esfahani | |
| 2010/0004662 A1 | 1/2010 | Ollivier | |
| 2010/0140125 A1 | 6/2010 | Mathiasen et al. | |
| 2012/0283518 A1 | 11/2012 | Hart | |

* cited by examiner

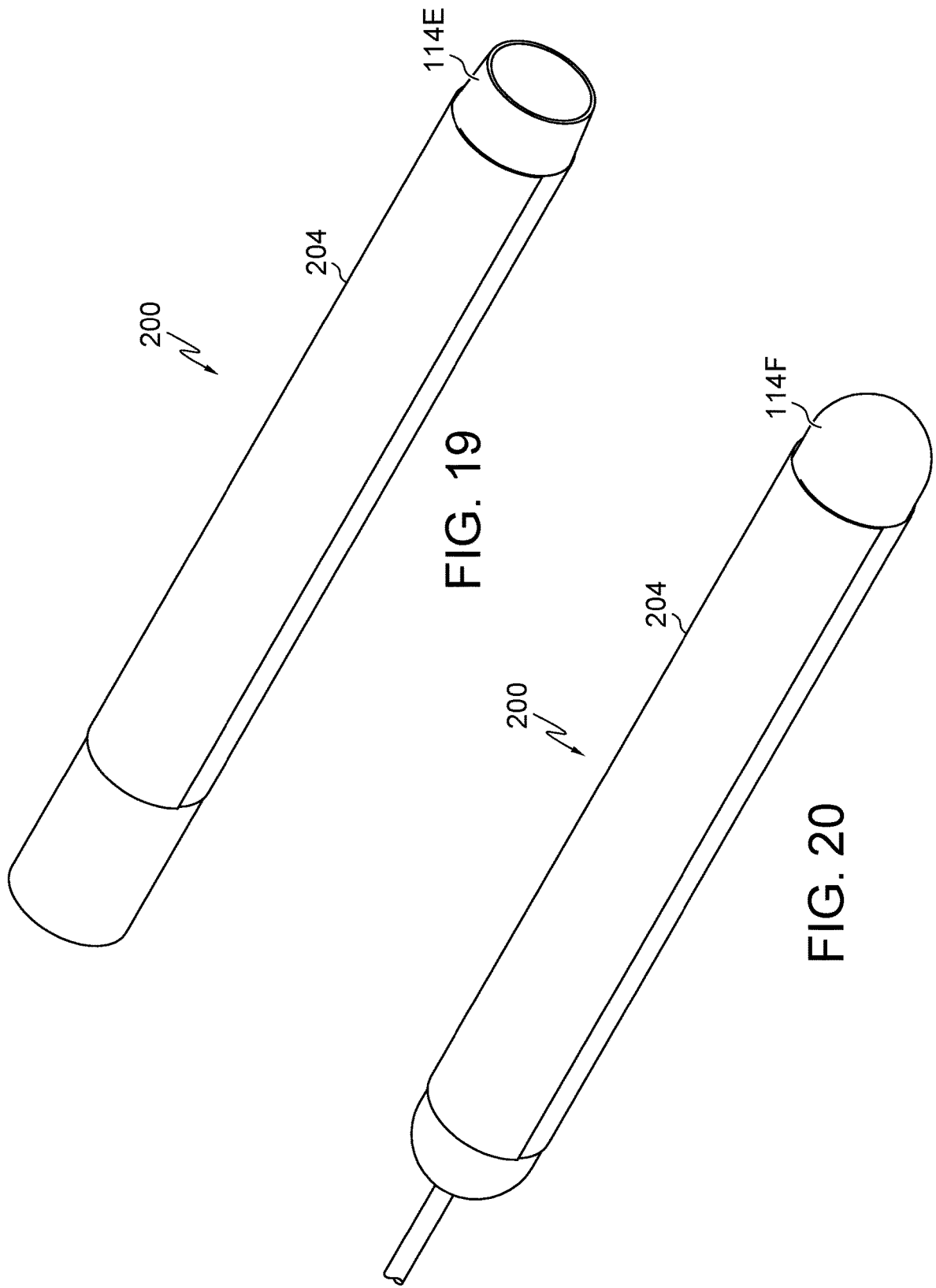

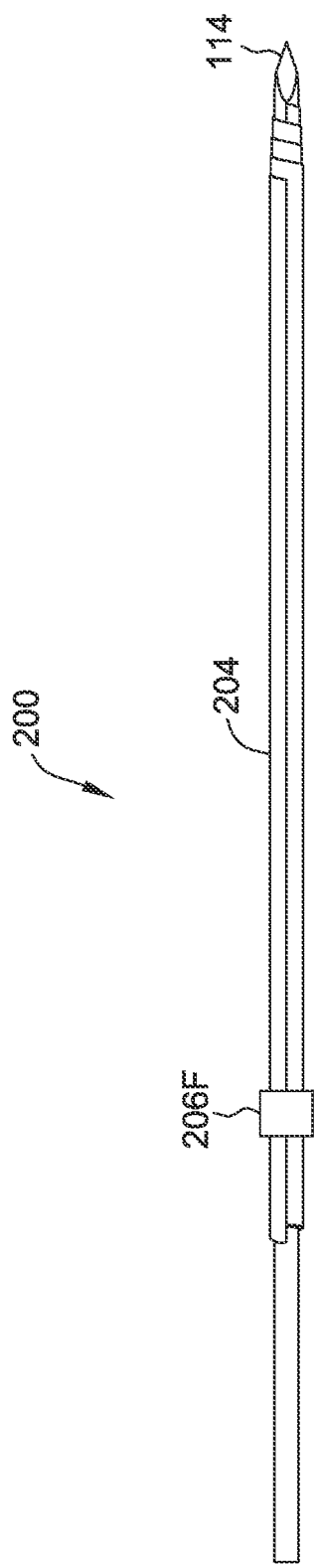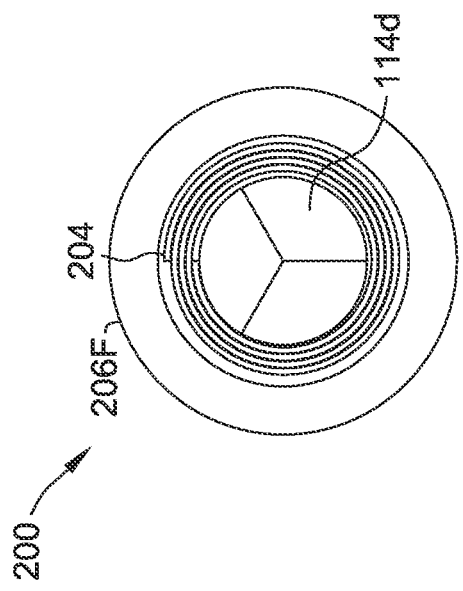
FIG. 45
FIG. 46

EXPANDABLE ACCESS SYSTEMS AND METHODS

CROSS REFERENCE TO RELATED APPLICATIONS

This non-provisional application is a continuation of U.S. patent application Ser. No. 13/683,847 filed Nov. 21, 2012, the entire contents of which are hereby expressly incorporated by reference into this disclosure as if set forth fully herein.

FIELD

Embodiments may include systems and methods related to access devices, implants, expandable devices, and other medical devices or applications. Also, embodiments may be used for any non-medical application suitable for the structures, features, and methods disclosed herein.

BACKGROUND

The present disclosure relates to access devices, implants, expandable devices, and other medical devices, for example cannulas, needles, stents, scaffolds, fasteners, etc. Traditional access devices (i.e. cannulas) may include a straight, fixed diameter tube which a surgeon may use to maintain a passage to a desired access area in a body portion of a patient. Traditional devices may require the surgeon to make an incision and a straight, full depth access opening order to insert the access device into the body portion. This may result in unnecessary damage to good tissue in order to reach the access area. Also, traditional devices may be straight thereby prohibiting access around the numerous curves and passages throughout the body. Traditional devices may also be non-expandable or have features obstructing the passage of the access device, which may limit the introduction of objects through the access device. It would be desirable to provide access devices which may not require a straight, full depth incision, may be introduced through a relatively small and/or natural opening in the body, may be navigated around natural curves and body passages, and/or allow access for objects.

SUMMARY

In accordance with the present disclosure, access, implant, expandable, and/or medical systems are provided herein. Systems or methods may have contracted and expanded configurations. For example, the system may comprise an expandable access device having a substantially helix or wrapped shape defining an access passage, a trocar having a trocar passage and being positionable in at least a portion of the access device, and/or a sleeve disposed over at least a portion of the access device and configured to resist radial expansion of the access device. Expansion of the trocar may radially expand the access device from the contracted configuration toward the expanded configuration.

In accordance with another feature of the present disclosure, systems or methods may comprise an expandable access device having a substantially wrapped shape and an access passage, an expandable trocar having a trocar passage and being positionable in at least a portion of the access device, and/or a sleeve disposed over at least a portion of the access device and configured to resist radial expansion of the access device. The access device may expand upon passage of a portion of an object in the access passage.

In accordance with a further feature of the present disclosure, systems or methods may comprise an expandable access device having a substantially helix shape about an access passage, a funnel connected to the access device, and/or a band disposed around at least a portion of the access device. The access device may expand from the contracted configuration toward the expanded configuration with release of the band.

In accordance with still another feature of the present disclosure, systems or methods may comprise providing an expandable access device with a substantially helix or wrapped shape, providing an expandable trocar in at least a portion of the access passage, positioning the expandable access device and trocar in a body portion of a patient, and/or expanding the trocar and access devices from the contracted configuration toward the expanded configuration.

Additional embodiments of the present disclosure are provided throughout this disclosure including the accompanying drawings.

BRIEF DESCRIPTION OF THE DRAWINGS

A more complete understanding of the present embodiments, and some of the attendant advantages and features thereof, will be more readily understood by reference to the following detailed description when considered in conjunction with the accompanying drawings.

FIG. 1 illustrates an embodiment of the present disclosure, for example, including an expandable device and/or a helix or spiral configuration.

FIG. 19 illustrates an additional embodiment of the present disclosure, for example, including a hollow or tubular introducer.

FIG. 20 illustrates an additional embodiment of the present disclosure, for example, including a balloon introducer.

FIG. 45 illustrates a side view of the embodiment of FIG. 44.

FIG. 46 illustrates a leading end view of the embodiment of FIG. 44.

FIG. 57 illustrates the embodiment of FIG. 56, for example, including an expanded condition.

DETAILED DESCRIPTION

Figure 1:
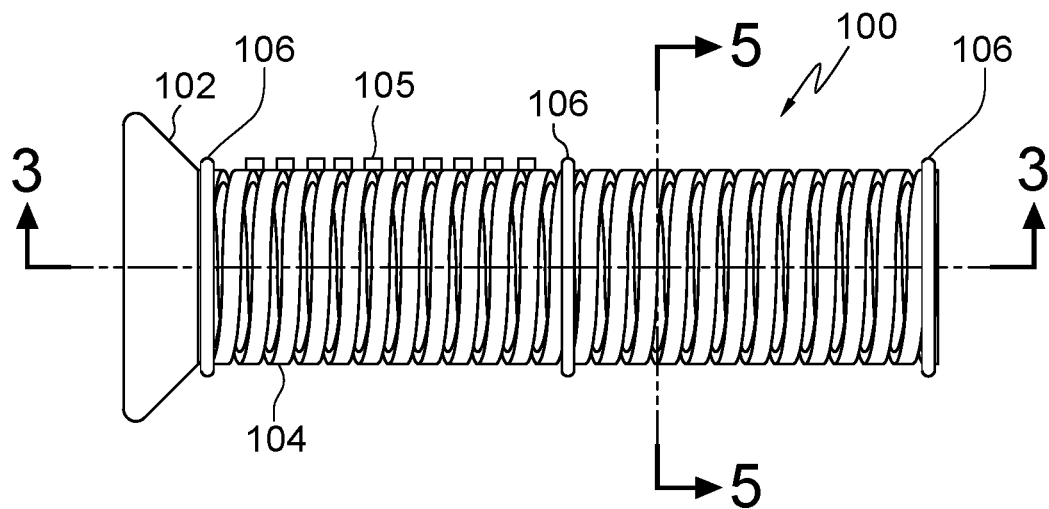
FIGS. 1-57 are provided as exemplary embodiments of the present disclosure, but it should be noted that any of the following figures may be used in conjunction with each other or any of the other embodiments of disclosed herein.

Embodiments may include a system for providing expansion, access, or an implant with respect to a body portion of a patient. Embodiments may move an object, fluid, substance, implant, and/or instrument into and/or out of a portion of a body of a human or another animal. Embodiments may include partially or entirely radially, linearly, asymmetrically, and/or telescopically expandable structures. Embodiments may include a partially or entirely bent, bendable, non-linear, and/or anatomically appropriate length and/or curvature, which may be associated with a depth of a portion of the body beneath a tissue surface. Systems may include a cannula, catheter, needle, stent, fastener, or any device configured to provide a passage, access, and/or support with respect to a portion of a body. Embodiments may be partially or entirely covered by a sleeve, band, and/or surface features. Embodiments may be used to position any object including medical implants and instruments.

The methods and devices disclosed herein may be used in conjunction with any medical procedure on the body, for example, related to any joint, bone, muscle, ligament, tendon, cartilage, capsule, cavity, vessel, duct, passage, organ, skin, nerve, vessel, or other body parts. As further examples, embodiments herein may be used during intervertebral disc surgery, kyphoplasty, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, shoulder surgery, hernia repair surgery, and surgery of an intrasubstance ligament tear, annulus fibrosis, fascia lata, or flexor tendons. In addition, embodiments may be used for applications related to biliary ducts, bronchi (i.e. cystic fibrosis), kidney stones, bile ducts, sinuses (i.e. sinusitis), small or large intestines (i.e. diverticulitis), bone cavities, vasculature, or any other site in the body that contains a passage or cavity or requires access. Embodiments may be expanded to provide a short or long term tissue support and/or degrade or absorb into tissue (i.e. stent absorbing into a blood vessel wall), for example, to facilitate tissue healing.

Embodiments may be configured to be an implant and/or be configured to receive and/or or position an object, instrument, and/or implant. The implant (i.e. stent) may be positioned over an expandable device thereby allowing the device to radially expand and place the implant with respect to a portion of a body (i.e. blood vessel). The implant may include a coronary artery stent, vascular stent, peripheral vascular stent, urinary tract stent, and/or urethral stent. Embodiments may include a partial or total knee replacement, hip replacement, shoulder replacement, bone fastener, etc. The implant may be an organ, partial organ grafts, tissue graft material (i.e. autogenic, allogenic, xenogenic, or synthetic), collagen, a malleable implant like a sponge, mesh, bag/sac/pouch, collagen, or gelatin, or a rigid implant made of metal (porous or nonporous), polymer, composite, or ceramic. Collagen or other materials disclosed herein may provide the benefit of bolstering tissue growth. Additionally, a desiccated collagen may be used to absorb surrounding fluid, which may provide the additional benefit of applying pressure on the tissue being repaired. Other implants include breast implants, biodegradable plates, porcine or bovine patches, metallic fasteners, compliant bearing for medial compartment of the knee, nucleus pulposus prosthetic, stent, fastener, suture, suture anchor, tissue graft, or tissue scaffold (i.e. biodegradable, collagen, polymeric and/or biocompatible scaffold).

The scaffold may include a collagen matrix configured to receive viable cells of any type. The matrix may be utilized as a support structure for cells. Different types of cells may be placed at various locations in the matrix. The matrix may be positioned relative to and/or any portion of a patient's body, for example all or any portion of a heart, blood vessel, brain, intestine, stomach, adrenal gland, liver, pancreas, bone, skeleton, spinal cord, or any other organ or any soft or hard tissue. The cell types may include progenitor cells which differentiate and proliferate to form cells having desired characteristics, stromal cells which relate to foundation supporting tissue, and mesenchymal cells which relate to connective tissues, blood and blood vessels, and other systems. Fibroblasts may be used in the production of connective tissues. Osteoblasts may be used in the production of hard tissue (i.e. bone). Myoblasts may be used in the production of muscle. Specific cells may be used to provide for growth of tissue having a function associated with the cell, which may include reticular cells, smooth muscle cells, chondrocytes, retinal cells, endothelial cells, fetal cells, stem cells, embryonic cells, adult cells, enzymes, proteins, and/or other cells known in the art. Once the viable cells have been positioned on the matrix, the result is a replacement tissue (i.e. an organ). Embodiments of the present disclosure may include the additional devices and methods disclosed in U.S. Pat. No. 7,299,805, entitled "Scaffold and Method for Implanting Cells", which is hereby incorporated by reference in its entirety.

Embodiments may include therapeutic substances, for example, to promote healing. These substances could include antibiotics, hydroxyapatite, anti-inflammatory agents, steroids, antibiotics, analgesic agents, chemotherapeutic agents, bone morphogenetic protein (BMP), demineralized bone matrix, collagen, growth promoting materials or surfaces (i.e. porous materials or pores), growth factors, autogenetic bone marrow, progenitor cells, calcium sulfate, immunosuppressants, fibrin, osteoinductive materials, apatite compositions, germicides, fetal cells, adult cells, stem cells, enzymes, proteins, hormones, cell therapy substances, gene therapy substances, and combinations thereof. These therapeutic substances may be combined with the materials used to make the device. Alternatively, the therapeutic substances may be impregnated or coated on the device. Time-released therapeutic substances and drugs may also be incorporated into or coated on the surface of the device. The therapeutic substances may also be placed in a bioabsorbable, degradable, or biodegradable material, for example a polymer. Therapeutic substances may be placed in one or more layers for incremental and/or controlled release.

Embodiments herein may include any biocompatible materials or other materials suitable for medical use. Embodiments may include portions and/or combinations of metals and polymers. Embodiments may include shape memory alloys (SMA) and/or shape memory polymers (SMP). Examples of amorphous polymers are polycarbonate (LEXAN), polystyrene, polysulfone (ULDALL), and acrylics polycarbonate (ABS and styrenes). Examples of semi-crystalline polymers include acetyl (DELRIN), nylon, polyester, polyethylene, polyether ether ketone, polypropylene, polyvinylchloride (PVC), and Caprolactam. Biodegradable semi-crystalline polymers may include polylactic acid and polyglycolic acid. Copolymers of PGA and PLA may also be used. Poly-l-lactide (PLLA) or other forms of PLA may also be used. Other polymers which may be used with the present invention, either as a thermoplastic or non-thermoplastic, are polyethylene glycol (PEG)-copolymers and D,L-lactide-co-glycolide polyesters. Some semi-crystalline materials are particularly suitable for surgical bonding and/or staking, especially vibratory bonding and staking. Examples of such materials include PAEK (polyaryletherketone), including PEEK (polyetheretherketone) and PEKK (polyetherketoneketone). Metals include stainless steel, shape metal alloys, tantalum, porous tantalum, titanium, and cobalt-chrome alloys. Shape memory alloys may include nitinol (nikel-titanium). Shape memory polymers may include PEEK, PMMA, and thermoset polymers. Thermoset polymers may include polyurethanes, polyethylene terephthalate (PET), polyethyleneoxide (PEO), block copolymers containing polystyrene and poly(1,4-butadiene), and ABA tri-block copolymers, for example including poly(2-methyl-2-oxazoline) and polytetrahydrofuran. Ceramic materials (i.e. implants) may include silicon nitride, alumina (aluminum oxide), and zircon (zirconium dioxide). Embodiments may include materials configured to resist growth of bacteria and/or biofilm, for example silicon nitride.

Embodiments may be any of biocompatible, degradable, biodegradable, bioerodible, bioabsorbable, mechanically expandable, hydrophilic, bendable, deformable, malleable, riveting, threaded, toggling, barded, bubbled, laminated, coated, blocking, pneumatic, one-piece, multi-component, solid, hollow, polygon-shaped, pointed, self-introducing, mesh, segmented, tubular, braided, suture material, elastic (i.e. rubber, silicone, or elastic materials), and combinations thereof. Furthermore, embodiments may include any of a metallic material, polymeric material, ceramic material, composite material, body tissue, synthetic tissue, hydrophilic material, expandable material, compressible material, bondable material, and combinations thereof. Embodiments may also include polymethyl methacrylate (PMMA or "bone cement"), glue, adhesive, grouting agents, acrylic materials, and combinations thereof.

Embodiments may be partially or entirely flexible, curved, non-linear, bendable, and/or may have shape memory properties or materials, which may allow all or any portion of the system to change in shape. A change in shape may include a change in angle, which may range between about 0-180 degrees. Use of a shape memory material may allow the angle to vary within a range of about 0-180 degrees with a change in temperature and/or by the application of heat. Embodiments may be shaped and/or positioned to access a curved or natural path through a body of a patient.

All or any portion of the system may be shaped, assembled, bonded, and/or positioned with energy, magnetic field, chemical reaction, mechanical interlocking, application of force, adhesives, and/or solvents. Energy may include thermal energy, resistive heating, radiofrequency (RF), vibratory energy (i.e. ultrasonic energy), microwave, laser, magnetic, electromagnetic, electro shockwave therapy, and/or plasma energy (hot or cold).

For this application, "bond", "bonded", and "bonding" includes, but is not limited to, attaching, engaging, connecting, binding, adhering, and/or fastening one or more materials through resistive heating, mechanical interlocking, application of force, application of grouting agents (i.e. bone cement), adhesives and/or solvents, spraying, radiofrequency, vibratory energy (i.e. ultrasound), microwave, laser, magnetic, electromagnetic, electro shockwave therapy, plasma energy (hot or cold), and any other method described herein.

Embodiments may include bondable materials. A bondable material may include any material that can soften and/or melt with the application of energy. Upon application of energy, bondable materials may become gel-like, tacky, and/or soft. The energy source and the technique used to bond and/or stake the material within the body can be selected to minimize or avoid damage to surrounding body tissue. Exemplary bondable materials that may be used may include polymers, PMMA, ceramics, composites, metals, and combinations thereof.

Vibratory energy may be used to bond a portion of the devices or systems herein to any portion of the devices, systems, or body areas disclosed herein. Embodiment may include or be coated in a bondable material then be positioned in a desired shape or location, for example in a desired access area. Application of ultrasonic energy may cause portions having bondable material to change in shape and/or bond to each other, another implant, and/or body tissue. For example, a helical or wrapped access device including a bondable material may be positioned and expanded at the access area, then vibratory energy may be applied to the access device to cause portions of the access device to bond and/or conform to itself, another implant, and/or tissue of the access area. Thus, the access device may be secured in the expanded condition and/or provide a passage, support, and/or an intraoperatively customized implant to the access area. Embodiments of the present disclosure may include any additional devices and methods disclosed in any of U.S. patent application Ser. Nos. 11/416, 618, 11/671,556, 11/689,670, 12/202,210, and 12/711,540, which are hereby incorporated by reference in their entirety.

Embodiments may include, be coated with, and/or provide bacteriacides or be configured to provide bacteriacides to a portion of the body. Bacteriacides include any agent that kills bacteria or slows or resists the growth or reproduction of bacteria, for example disinfectants, bacterial antiseptics, bacterial antibiotics, or any combination thereof. Embodiments may include an injection and/or suction port, for example, to inject bacteriacides and/or remove unwanted materials.

Embodiments may include any or all of a cannula, sleeve, band, introducer, trocar, and/or implant. All or any portion of the system may have a passage and/or be expandable and/or bendable. An object may be positioned over, in, or through all or any portion of the system. As used in the present disclosure, an object may include an instrument, implant, dilator, trocar, introducer, imaging device, or any other device or material disclosed herein.

One or more sleeves and/or bands may provide radial resistance to the expansion of the cannula, which may be overcome by cutting the band and/or positioning an introducer therein. Expansion of the cannula and/or sleeve may deploy and/or expand the implant. All or any portion of the system may be configured to provide any or all of air, water, sterile fluid, disinfectant, and therapeutic substance. A method may include providing a fluid to a body structure (i.e. blood vessel), positioning an implant (i.e. endovascular stent), and/or passing an instrument into a body structure via the system.

Figure 57:
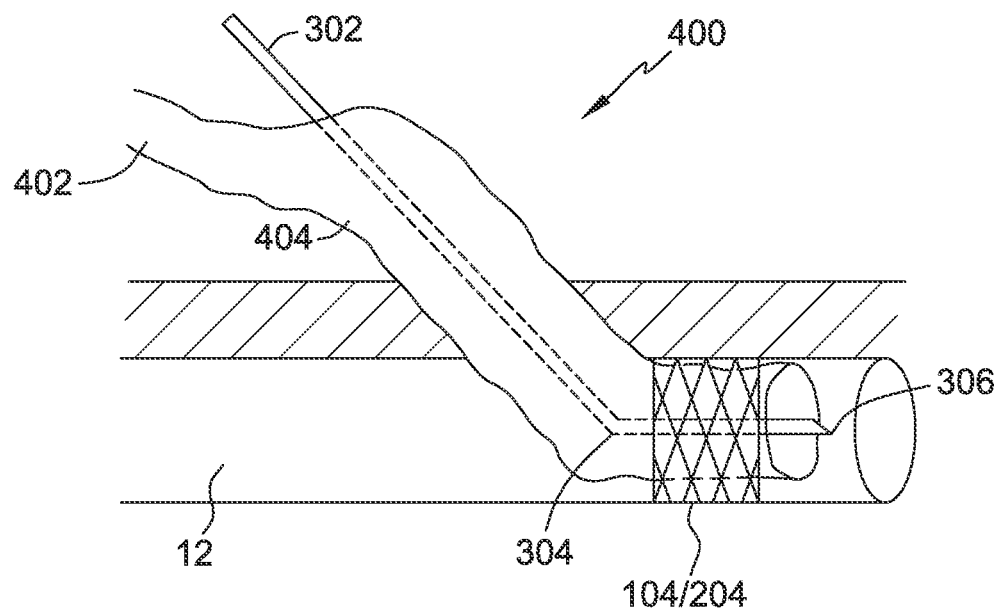

Referring to FIGS. 1-57, embodiments may relate to expandable devices, access devices, implantable devices, combinations thereof, and any other medical devices. System 100/200 may include any or all of the features disclosed herein, for example opening 102, body 104/204, support 105, band 106, valve 108, sleeve 110, trocar 112, introducer 114, band 206, rib 216, feature 218, and/or wire 220. All or any portion of any embodiment herein may be expandable, bendable, implantable, and/or configured to access a portion of a body of a human or other animal. Any of the systems herein may include a passage configured to pass an object through all or any portion of the system.

Figure 2:
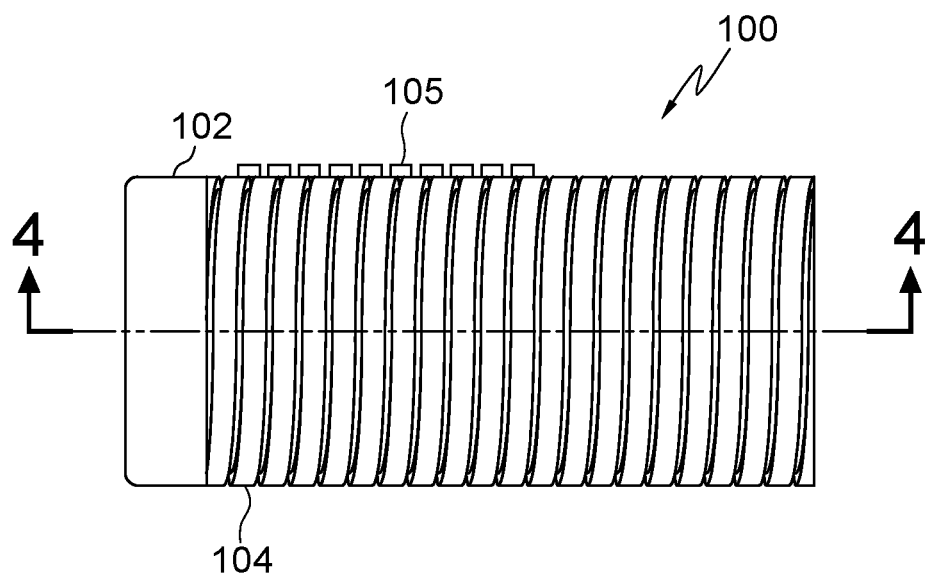
FIG. 2 illustrates the embodiment of FIG. 1, for example, in an expanded configuration.

Any or all of system 100/200 may be expandable from a contracted configuration (i.e. FIG. 1) to an expanded configuration (i.e. FIG. 2). Alternatively, system 100/200 may be contract from the expanded configuration to the contracted configuration. Embodiments may be positioned in the body in either the contracted or expanded configuration. Expansion and/or contraction may occur prior to, during, and/or after being positioned in or removed from the body. Embodiments may be expandable within any size range, for example from a contracted configuration having about a about a 2 to 3 mm diameter (i.e. 2 mm) diameter passage to an expanded configuration having a passage diameter of about or between any of 4.5, 5, 12, 13, and/or 15 mm. System 100/200 may have a working length of about or between any of 70, 110, 150, and/or 160 mm.

Figure 13:
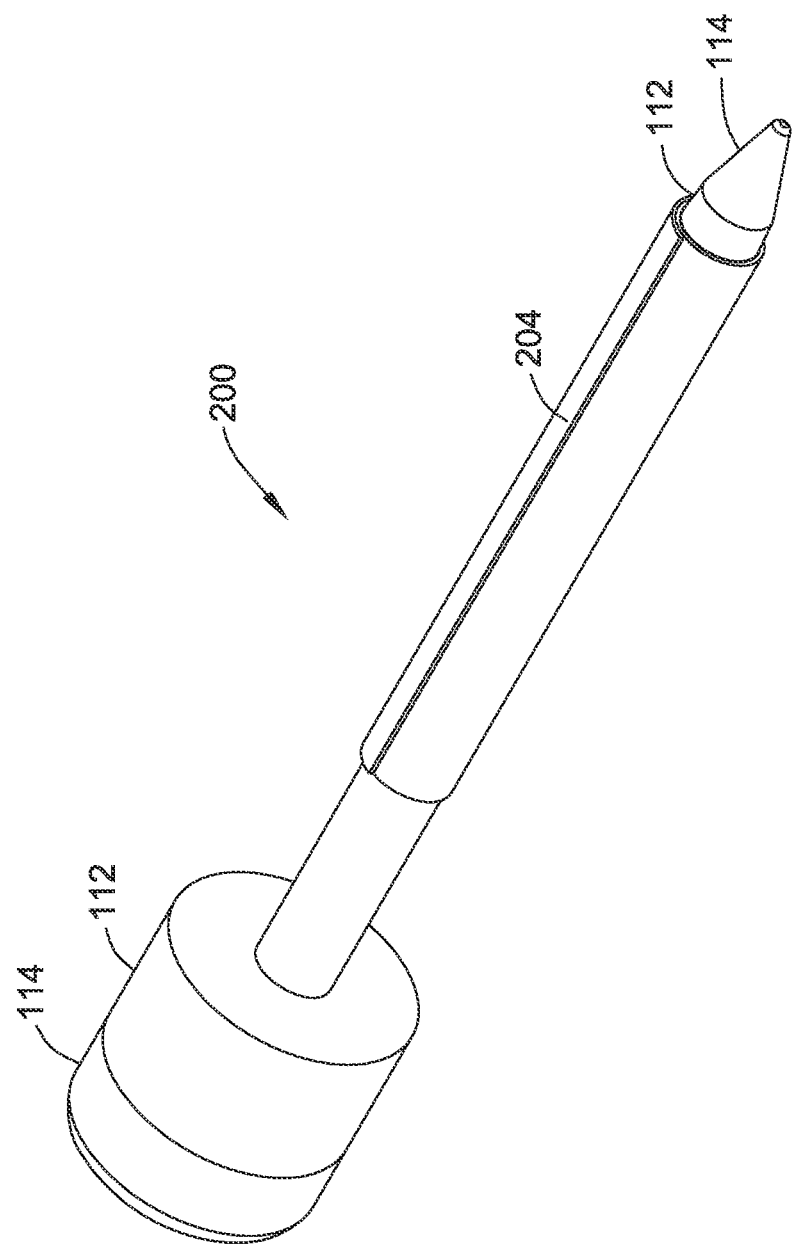
FIG. 13 illustrates an additional embodiment of the present disclosure, for example, including a wrapped configuration.

Embodiments may include opening 102, which may be any shape configured for expansion, access, and/or implantation. (FIG. 1) Opening 102 may include a funnel having a conical entrance or any shape suitable to direct an object into body 104/204, which may be expandable and/or pivot with respect to body 104/204. Body 104/204 may include an elongate, tubular, cylindrical, spiral, helical, or wrapped shape. (FIGS. 1-57). Body 104 may include a spiral or helical shape that may be formed with a cut, for example a helical laser cut about an axis of the passage. (FIG. 1) Alternatively, the spiral or helical shape of body 104 may be formed with a wire rolled into a spiral or helical configuration. (FIG. 1). In another embodiment, body 204 may include a sheet that may be rolled, wrapped, or overlapped. (FIG. 13). Body 104/204 may include a plurality of rings, filaments, and/or longitudinal, radial, overlapping, or asymmetrical elements. The shape of body 104/204 may also include a mesh, diamond, polygon, z-shaped, or zig-zag pattern, which may be on the surface or cut through body 104/204.

Embodiments may include connector 105 and/or band 106/206, any of which may be elastic, expandable, and/or resist expansion of body 104/204. (FIG. 1). Connector 105 and/or band 106/206 may be cut or broken, which may allow and/or control expansion. Connector 105 and/or band 106 may include a ring, tape, adhesive, glue, elastic, polymer, metal, tape, vibratory energy bond, and/or any other embodiments disclosed herein.

Figure 3:
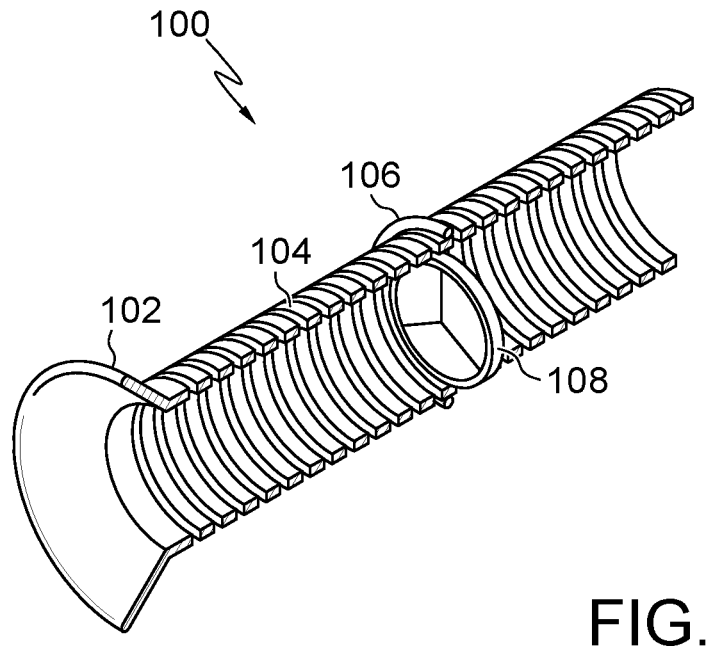
FIG. 3 illustrates a section view of an embodiment of FIG. 1.
Figure 4:
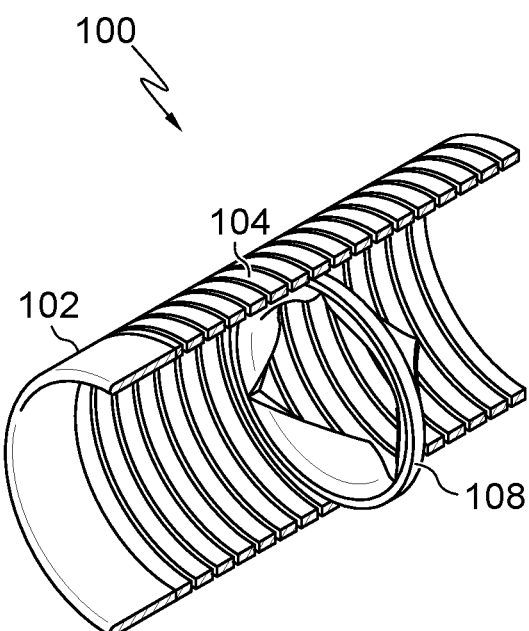
FIG. 4 illustrates a section view of an embodiment of FIG. 2.

Embodiments may include one or more valves 108 (FIGS. 3 and 4) and/or ports (not shown). Valve 108 and/or the port may be positioned at any location along system 100/200, for example along the passage of body 104/204. Valve 108 may be configured to seal or resist the movement of an object, fluid, or other items with respect to the passage. Valve 108 may include any number of flaps, for example, to obstruct all or any portion of the passage. The port may be configured to provide access for objects, fluids, instruments, and/or implants and/or be configured to increase or decrease pressure.

Figure 5:
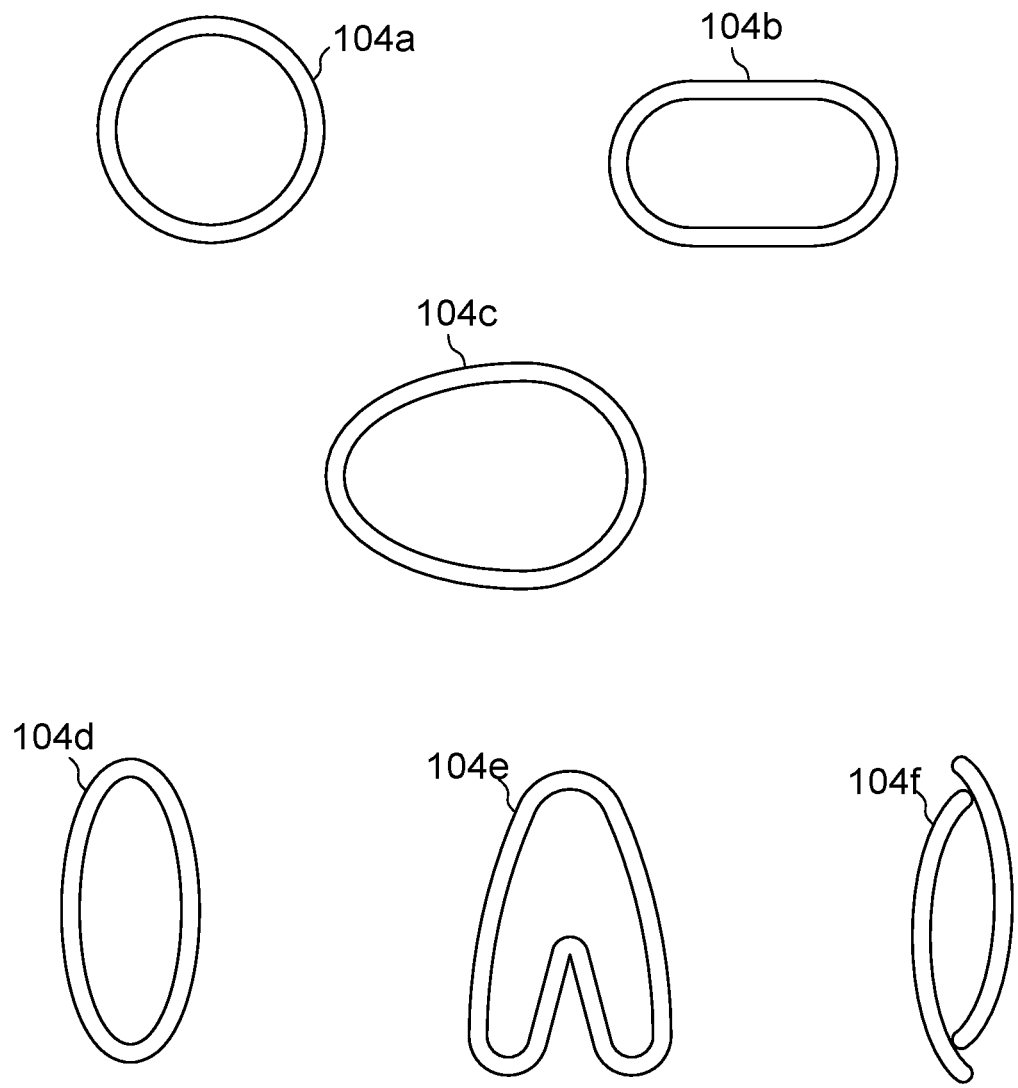
FIG. 5 illustrates example cross sections of embodiments of the present disclosure.
Figure 6:
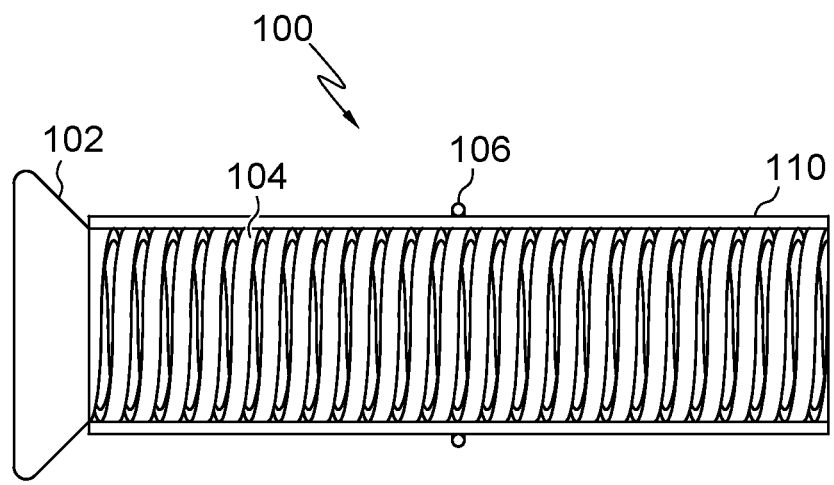
FIG. 6 illustrates an embodiment of the present disclosure, for example, including a band and/or sleeve.
Figure 7:
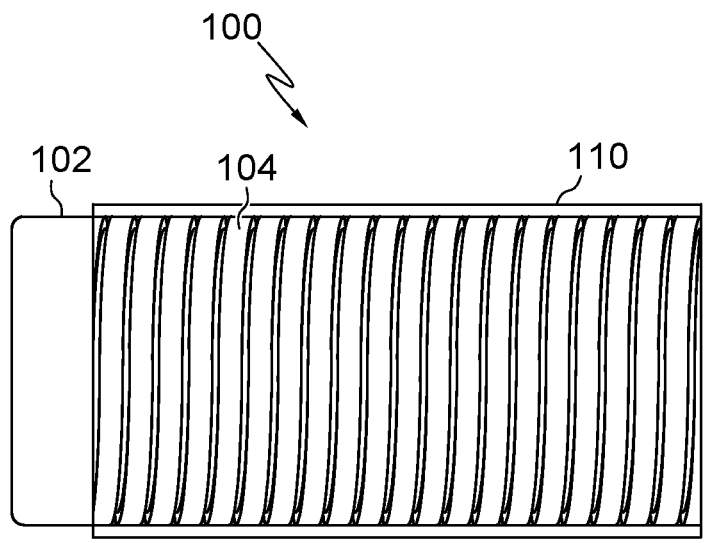
FIG. 7 illustrates the embodiment of FIG. 6, for example, in an expanded configuration.

Body 104/204 may include any number of elements or cross-sectional shape, for example body 104a-104f. (FIG. 5). The cross-sectional shape may change along the length of body 104/204. For example, a proximal end of body 104/204 may have a larger or smaller cross-sectional shape than a distal end of body 104/204. Embodiments may have a shape configured to facilitate positioning into the passage of body 104/204 and/or the leading end of body 104/204 may have a shape configured to access and/or approximate the specific anatomical surfaces of a body portion of the patient. (FIGS. 1 and 6). As a further example, the proximal end of body 104/204 may be configured to the shape of a proximal portion of an object and/or the leading end of body 104/204 may be configured to a leading portion of the object being positioned in the body. The shape and dimensions of body 104/204 may be configured for a specific patient, for example the length and/or shape of body 104/204 may be configured to specific anatomical surfaces of a specific patient and/or to provide access to a tissue or passage at a specific anatomical depth and/or location in a specific patient. Body 104/204 may be a unitary element or any number of interconnecting or separate elements (i.e. two, three, four, five, six, or more elements).

Vibratory energy may be used to shape or position body 104/204. Body 104/204 may include or be coated with a bondable material. Adjacent sections of body 104/204 may be bonded together with application of vibratory energy. In use, body 104/104 may be formed into a desired shape, then vibratory energy may be applied to secure body 104/204 to maintain the shape. As another example, body 104/204 may be positioned and/or expanded in a desired location in the body, then vibratory energy may be applied to body 104/204 to maintain expansion. Body 104/204 may be positioned in an expanded condition, then vibratory energy may be applied to contract body 104/204 for repositioning and/or removal.

Sleeve 110 may be positionable any portion or all of the system. (FIGS. 6-12). Sleeve 110 may be configured to span all or any portion of the system. All or any portion of sleeve 110 may be elastic, plastic, thermoplastic, any combination thereof, and/or any other material disclosed herein. As an example, the sleeve 110 may be configured as an elongate tubular member made of an elastic material. Sleeve 110 and/or introducer 114 may include a balloon. As further example, sleeve 110 may be heat-shrunk or ultrasonically bonded to conform to body 104/204. In use, sleeve 110 may facilitate insertion of system 100 into a portion of a body, be expanded by body 104/204 with insertion of introducer 114, and/or expand with air and/or fluid pressure.

Figure 8:
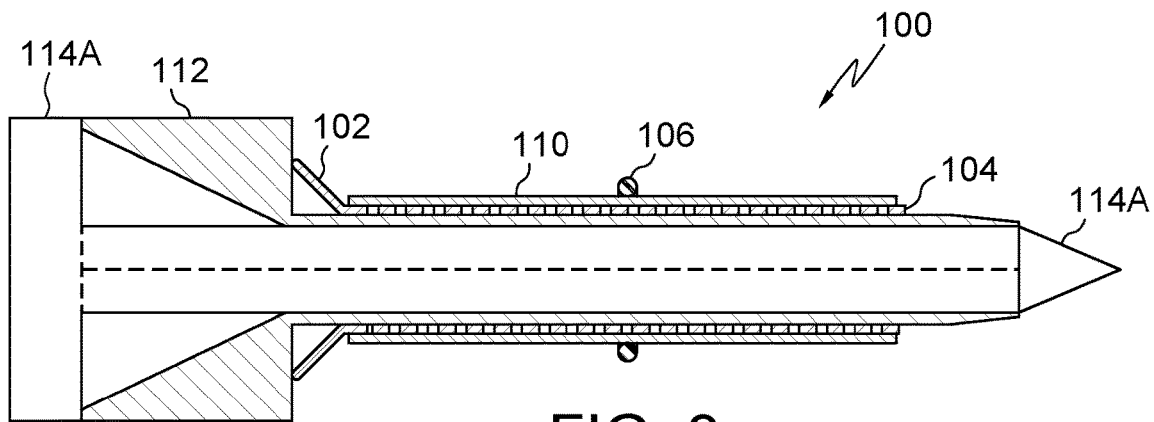
FIG. 8 illustrates an embodiment of the present disclosure, for example, including an expandable device, trocar and/or introducer.
Figure 9:
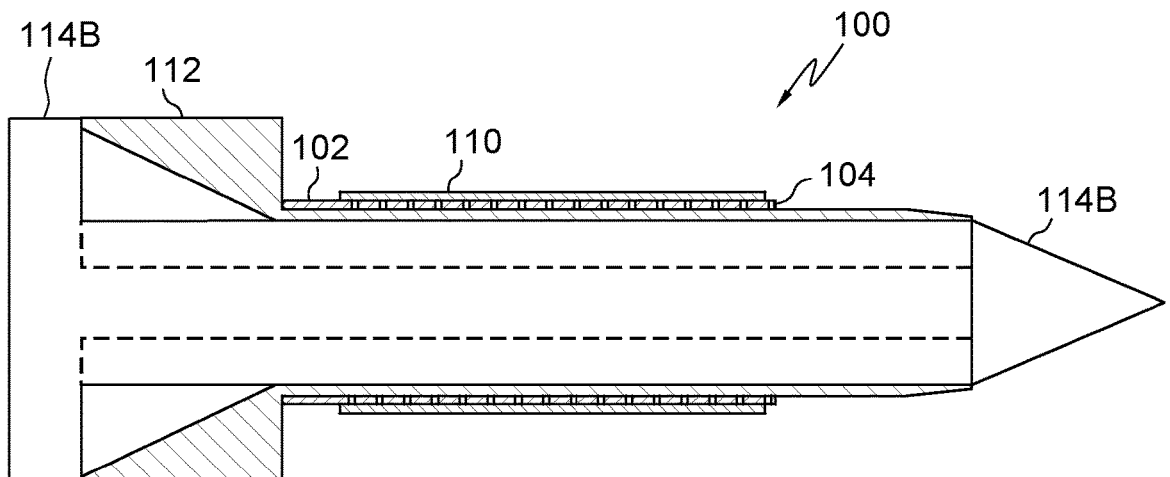
FIG. 9 illustrates another embodiment of the present disclosure, for example, including dilation of a passage.

Embodiments may include opening 102, body 104/204, sleeve 104, band 106, seal 108, a port (not shown), trocar 112, and/or introducer 114. (FIGS. 1-12). Opening 102 may facilitate positioning of trocar 112 and/or introducer 114 into the passage of sleeve 110. Trocar 112 and/or introducer 114 may have a tapered, sharp, and/or pointed leading end (FIG. 8), for example, to assist penetration into body 104/204, trocar 112, and/or a tissue of the body of the patient. Trocar 112 may be configured to be received by and/or positioned in a passage of body 104/204, sleeve 110 and/or introducer 114. Introducer 114B may include a series of dilators having two or more sizes, for example, to progressively expand the body tissue of the patient. (FIG. 9).

Figure 10:
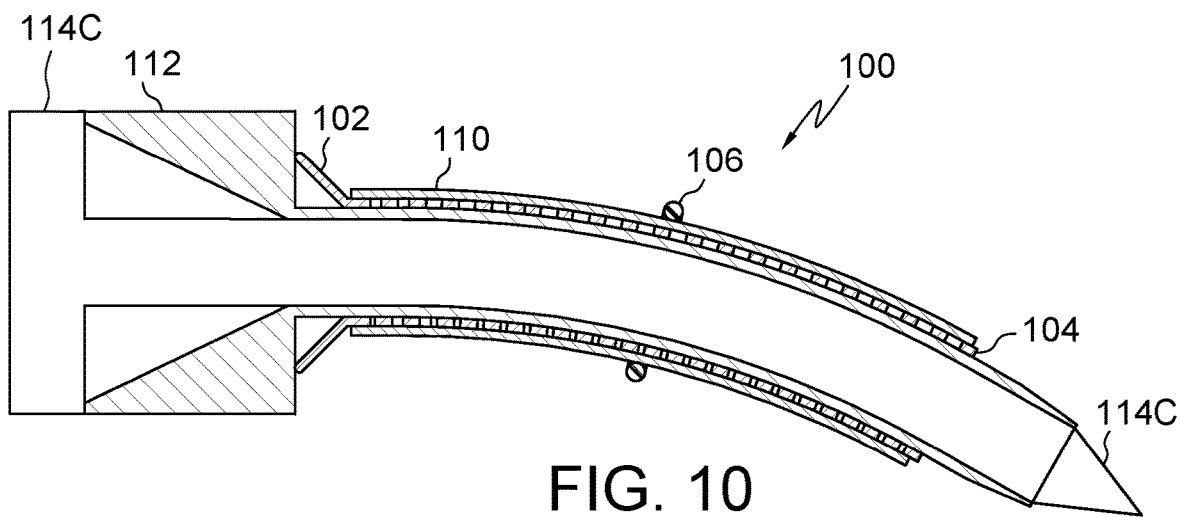
FIG. 10 illustrates another embodiment of the present disclosure, for example, a curved, non-linear, and/or bent configuration.

Body 104/204, trocar 112, and/or introducer 114 may include a curve or a curved portion. (FIG. 10). Body 104/204, trocar 112, and/or introducer 114 may be manufactured in a curved shape to approximate the anatomic curvature of the body or the curvature required to access a body passage. Body 104/204, trocar 112, and/or introducer 114 may be manually, magnetically, and/or robotically manipulatable and/or controllable. Body 104/204, trocar 112, and/or introducer 114 may include shape memory alloys and/or polymers, for example having a substantially straight configuration at near a first temperature (i.e. room or near skin temperature) and a substantially curved configuration at near a second temperature (i.e. temperature resulting from applied energy or internal body temperature). Body 104/204 also may be urged into a curved configuration with receipt of a curved trocar 112 and/or introducer 114C. Embodiments of the present disclosure may also include any devices and methods disclosed in U.S. patent application Ser. No. 10/102,413, "Methods of securing body tissue" and U.S. patent application Ser. No. 12/576,992, entitled "Stabilizing a Spinal Anatomical Structure", which are hereby incorporated by reference in their entirety.

Body 104/204, sleeve 110, and/or trocar 112 may be expandable and/or introducer 114 may be configured to be positioned in and/or expand body 104/204, sleeve 110, and/or trocar 112. (FIG. 8-10). Any or all of body 104/204, trocar 112 and/or introducer 114 may mechanically interlock with itself, each other, or another object, for example an instrument and/or implant may be configured to interlock with the system for positioning and unlock for removal of the instrument and/or deployment of the implant.

In use, body 104/204, sleeve 110, trocar 112, and/or introducer 114 may be urged toward a desired access area of the body. Introducer 114 may pierce tissue until a desired access area has been achieved. Introducer 114 may then be removed thereby exposing a passage through of trocar 112. An object may be positioned in the passage to expand trocar 112 thereby expanding body 104/204. Introducer 114A (FIG. 10) may be used to pierce tissue, then introducer 114B may be used to expand body 104/204 and/or trocar 112 thereby creating additional access with respect to a portion of the body of the patient. After the desired access has been created, trocar 112 may remain in position or be removed from the accessed area, then a procedure may be performed or an implant may be positioned through body 104/204. Body 104/204 may be left in the body of the patient as an implant if a longer term access and/or distraction of tissue is desirable.

Figure 11:
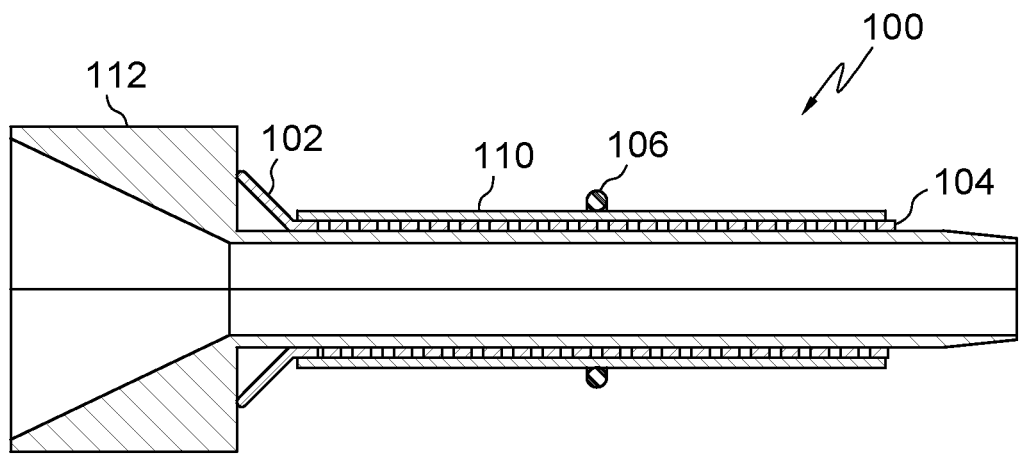
FIG. 11 illustrates an embodiment of the present disclosure, for example, including an expandable device and/or a trocar.
Figure 12:
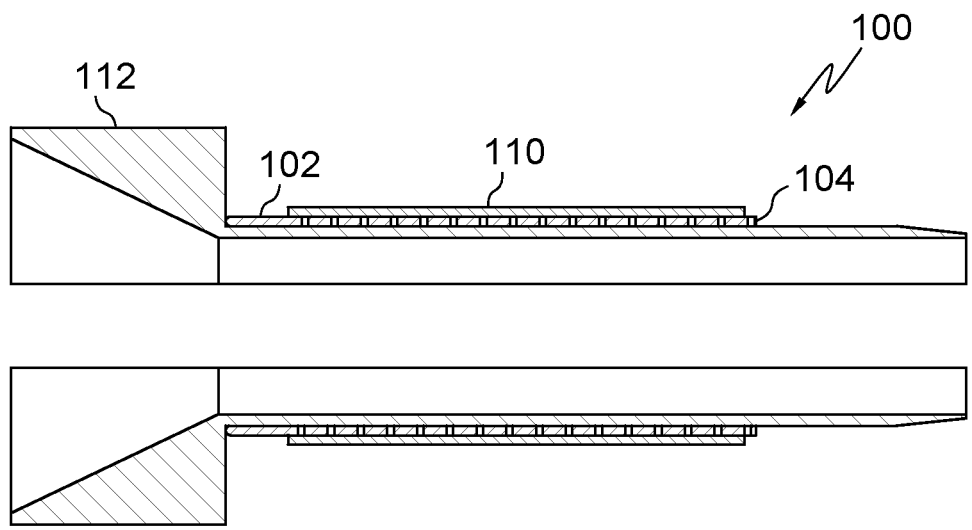
FIG. 12 illustrates the embodiment of FIG. 11, for example, including an expanded configuration.

Trocar 112 may be positioned in body 104/204 without introducer 114. (FIGS. 11-12). Trocar 112 may have a tapered, sharp, and/or pointed leading end (FIG. 11), for example, to assist positioning into body 104/204 and/or penetration of a body tissue of the patient. In use, body 104/204, sleeve 110, and/or trocar 112 may be urged toward a desired access area of the body. Trocar 112 may pierce tissue until a desired access area has been achieved. Trocar 112 may then be expanded and/or removed thereby providing a passage through body 104/204. An object may be positioned in the passage to expand body 112 thereby expanding body 104/204. After the desired access has been created, trocar 112 may remain in or be removed from the accessed area, then a procedure may be performed or an implant may be positioned through body 104/204. Body 104/204 may be left in the body of the patient as an implant or for longer term access, support, and/or distraction of tissue. Body 104/204 may be biodegradable for shorter term access, support, and/or distraction of tissue.

Referring to FIGS. 13-51, body 204 may include a rolled or wrapped configuration. Embodiments of body 104 and body 204 are contemplated to be interchangeable throughout this disclosure. All or any portion of body 204 may be rolled, wrapped, or overlapped in the non-expanded and/or expanded configurations. Body 204 may telescope, radially expand, and/or linearly expand. Body 204 may be rolled or wrapped for any number of turns in contracted and/or expanded configurations.

Figure 14:
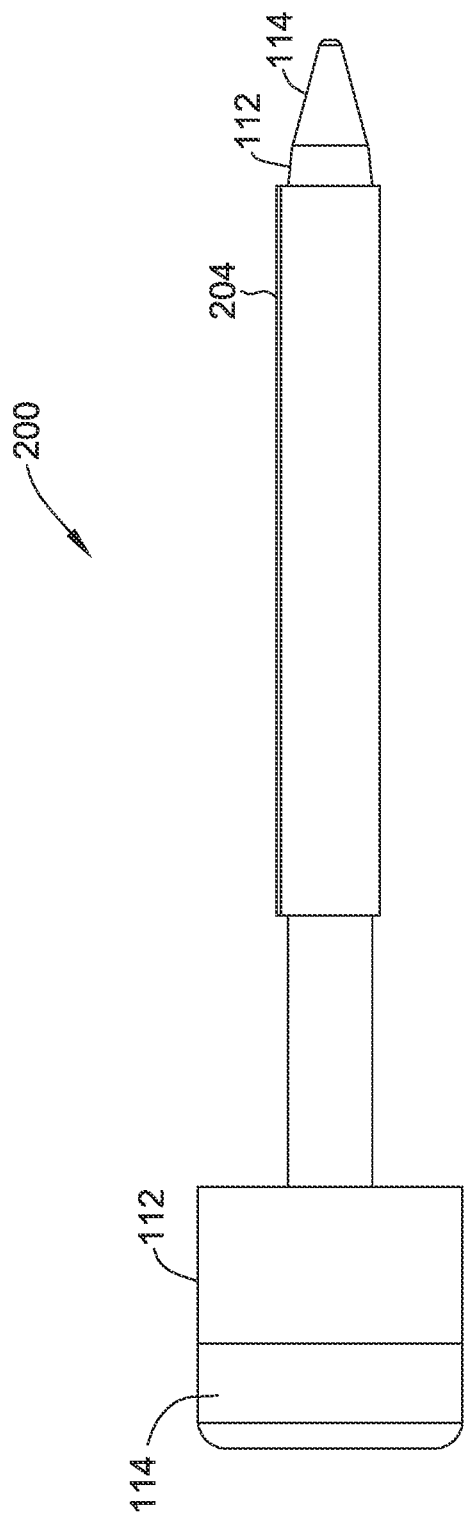
FIG. 14 illustrates a side view of the embodiment of FIG. 13.
Figure 15:
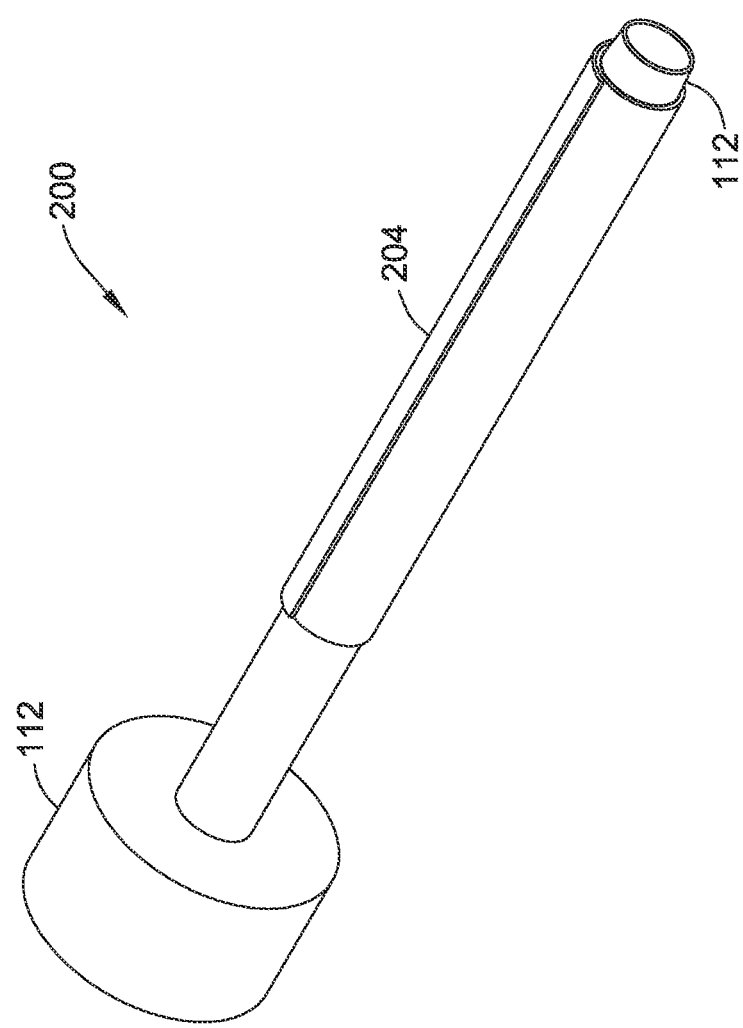
FIG. 15 illustrates an additional embodiment for FIG. 13.
Figure 16:
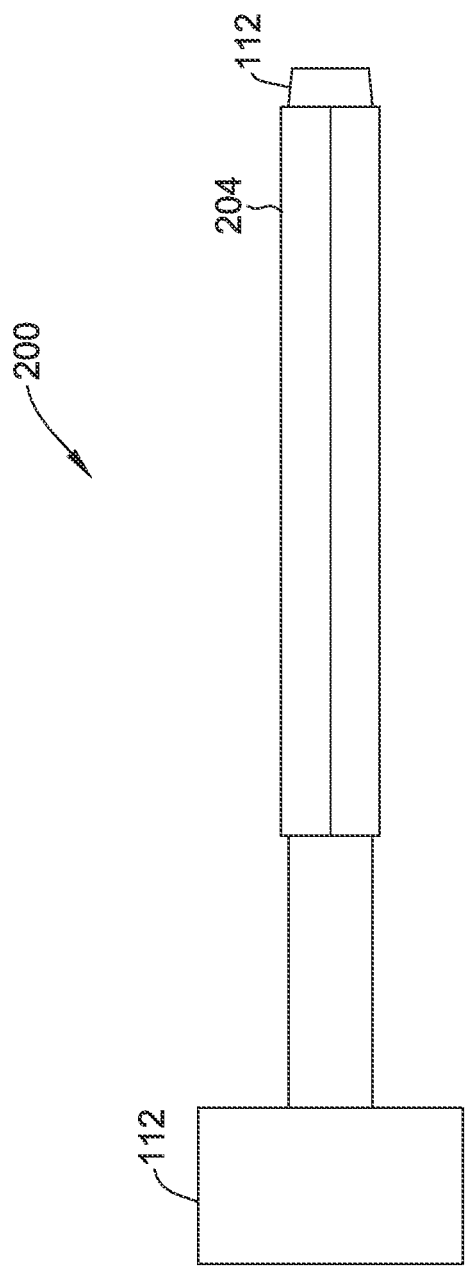
FIG. 16 illustrates a side view of the embodiment of FIG. 15.

Body 104/204 may be positioned over all or any portion of the length of trocar 112 and/or introducer 114, for example adjacent the leading end of trocar 112 and/or introducer 114 for deeper access. (FIGS. 13-14). Alternatively, body 104/204 and/or trocar 112 may be positionable without introducer 114 (FIG. 15-18).

Figure 17:
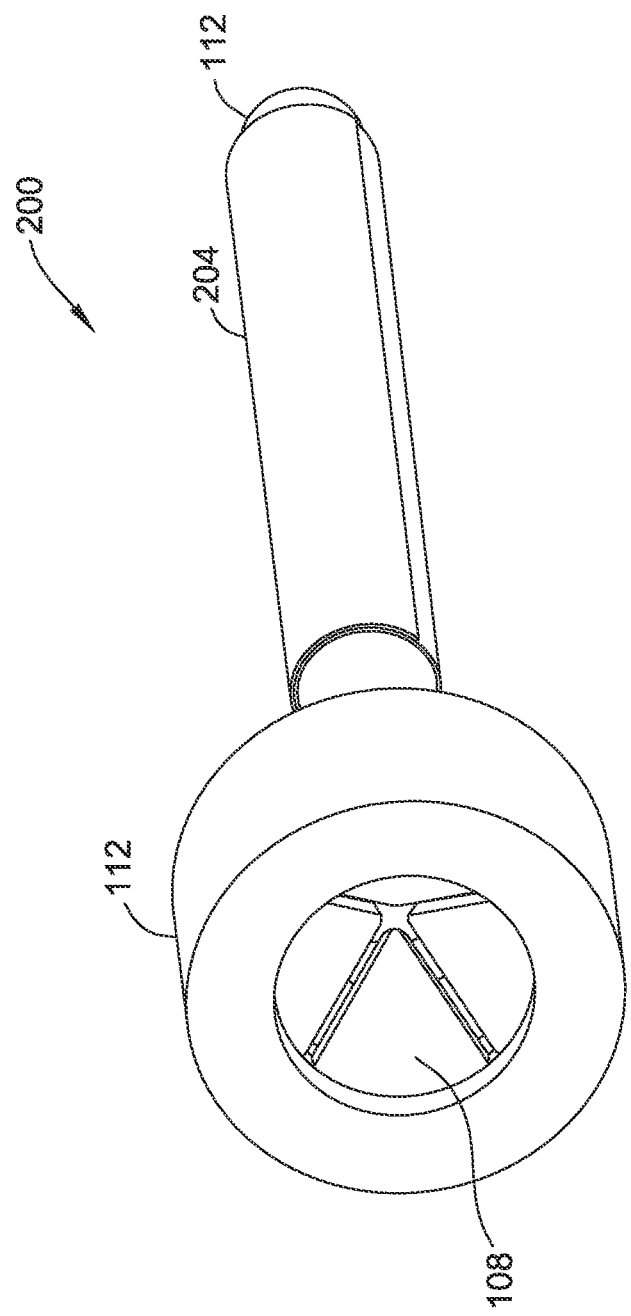
FIG. 17 illustrates an additional view of the embodiment of FIG. 15, for example, including a valve.
Figure 18:
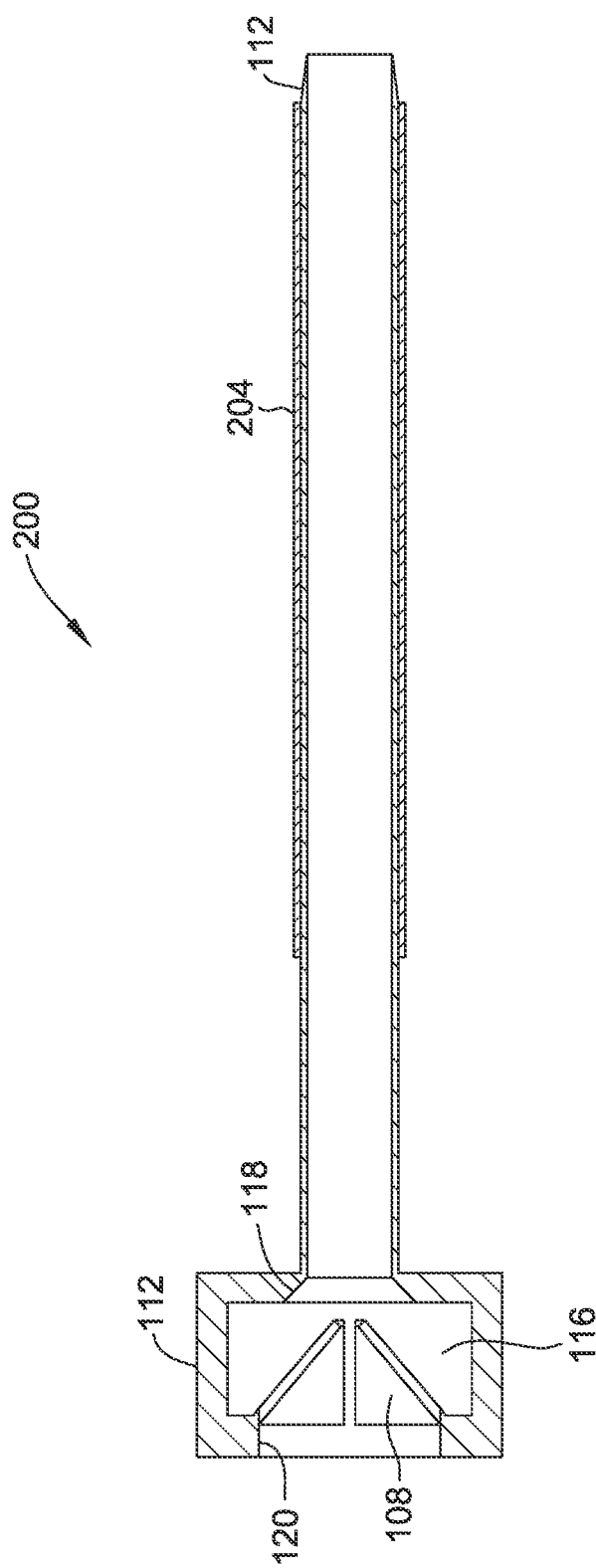
FIG. 18 illustrates a cross section view of the embodiment of FIG. 15, for example, including a chamber and/or chamfers.

Trocar 112 may have one or more valves 108, ports, and/or chambers. (FIG. 17-18) Valve 108 may have any number of flaps. (FIG. 17). Valve 108 may be along any portion of trocar 112, for example at a proximal end of trocar 112. Trocar 112 may include chamber 116, for example, to capture excess fluid. (FIG. 18). Trocar 112 may include surface 118 and/or surface 120, which may be chamfered and/or be configured to direct an object (i.e. instrument, implant, dilator, and/or introducer 114) toward the passage of trocar 112. Flaps of seal 108 may be anywhere along the length of trocar 112 or at any angle with respect to the passage axis, for example at the proximal end and angled around 30-90 degrees (i.e. approximately 45 degrees shown) toward the passage axis to direct objects toward the passage. (FIG. 18).

Figure 26:
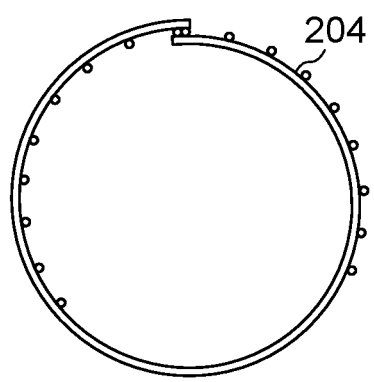
FIG. 26 illustrates an embodiment of the present disclosure, for example, including an expanded configuration.

Introducer 114 may have any shape or length. All or any portion of introducer 114E may be tubular or hollow. (FIG. 19). Introducer 114F may include a balloon or another fluid operated device, for example to control expansion of body 104/204, sleeve 110, and/or trocar 112 by increasing or decreasing pressure. (FIG. 26).

Figure 21:
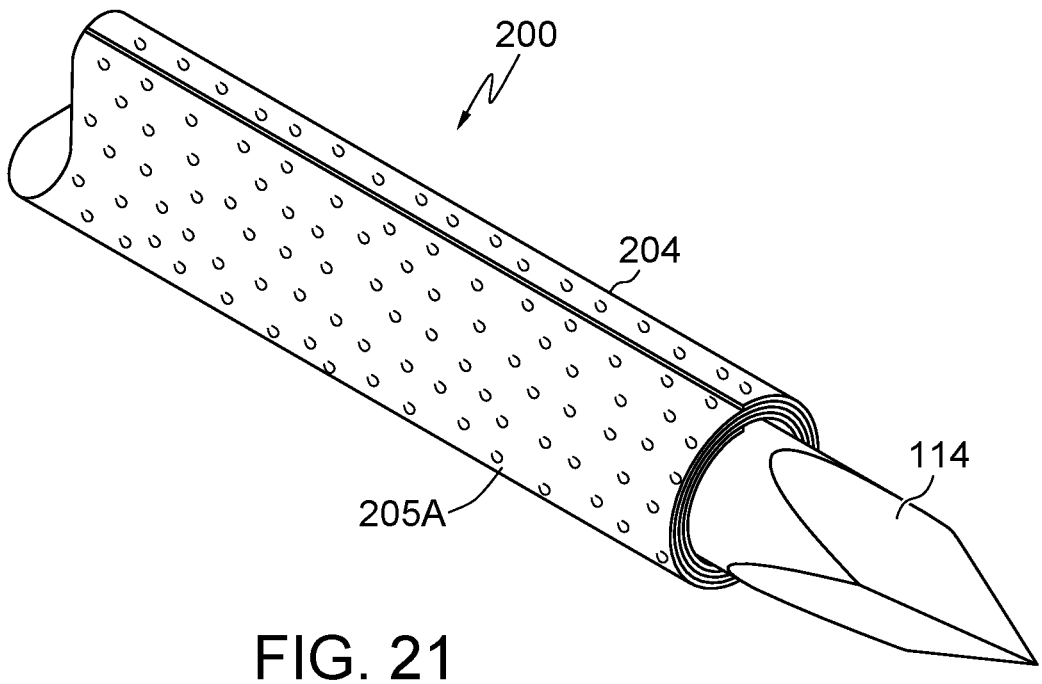
FIG. 21 illustrates an embodiment of the present disclosure, for example, including surface features, and/or a leading end.
Figure 22:
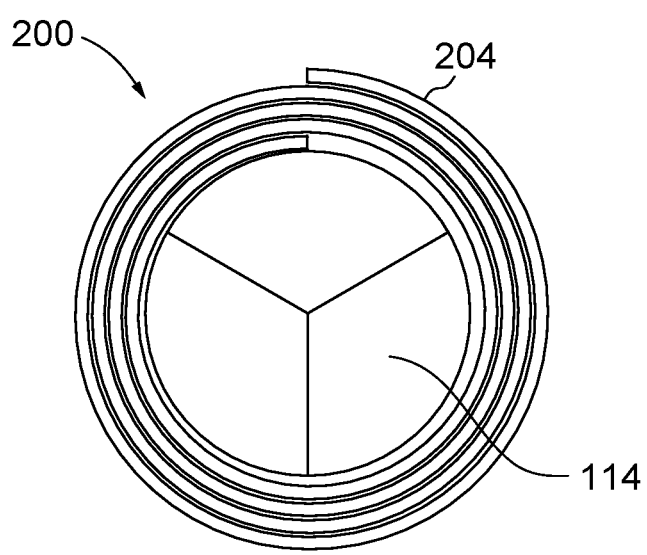
FIG. 22 illustrates a leading end view of the embodiment of FIG. 21.
Figure 23:
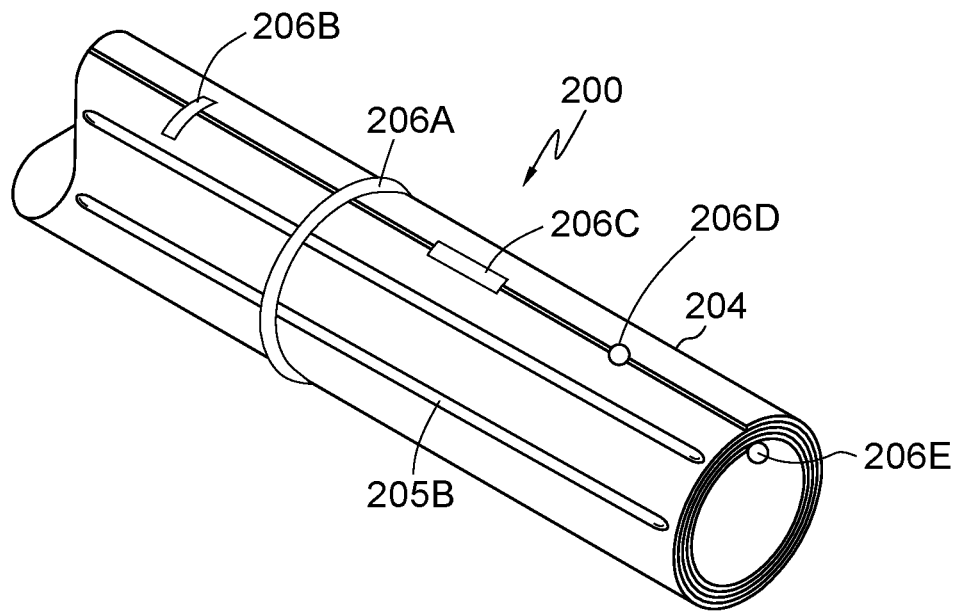
FIG. 23 illustrates an embodiment of the present disclosure, for example, including bands and/or surface features.
Figure 24:
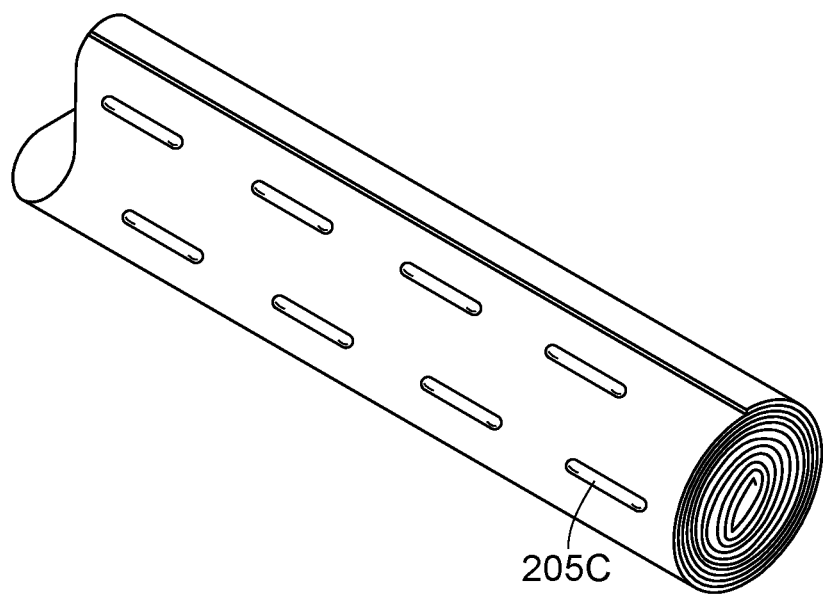
FIG. 24 illustrates an embodiment of the present disclosure, for example, including surface features and/or a fully wrapped configuration.

All or any portion of body 104/204 may include a surface feature 205. (FIG. 21-26). Surface feature 205 may be on an inner or outer surface of body 104/204. Embodiments may include natural and/or manufactured surface features. Embodiments may include one or types or locations having surface features. Surface feature 205A may include a porous surface, textured surface, dimples (i.e. recesses into the surface), bumps (i.e. protrusions out of the surface), holes, or slots. (FIG. 21). Surface feature 205B may include one or more ribs along the circumference and/or length of body 104/204. (FIGS. 23-24). Surface feature 205C may be positioned in one or more increments along the circumference and/or length of body 104/204. (FIG. 24). Surface feature 205 may be configured to grip and/or secure body 104/204 with respect to itself, sleeve 110, trocar 112, introducer 114, and/or a tissue of the body of the patient. (FIGS. 21-26).

Band 106/206 may be positioned around or along all or any portion of the circumference or length of body 104/204. (FIG. 23). Embodiments of band 106, band 206, and sleeve 110 are contemplated to be interchangeable throughout this disclosure. Band 106/206 may include a ring, tape, adhesive, glue, elastic, polymer, metal, tape, bonded with vibratory energy, and/or include any material disclosed herein. Band 206A may include a ring configured to resist outward radial expansion of body 104/204. Band 206B may have any polygonal shape (i.e. rectangular shown) and/or be positionable across an exterior portion of body 204, for example substantially perpendicular to an exterior end. Band 206C may be positionable along the exterior portion of body 104/204, for example substantially parallel to an exterior end of body 204. Band 206D may include any rounded shape (i.e. substantially spherical shown) and/or be positionable at any point on the exterior portion of body 204, for example the exterior end. Band 206E may be configured to resist inward radial contraction of body 204 and/or be positionable on an interior portion of body 204, for example an interior end. In addition, band 106/206 may include a hook, ratchet, tab, fastener, or ramp shape, for example, to secure and/or remove band 106/206.

Figure 25:
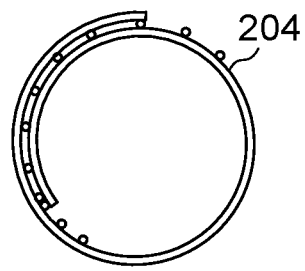
FIG. 25 illustrates an embodiment of the present disclosure, for example, including interior and/or exterior surface features.

Body 204 may be configured to overlap an interior portion having external surface ribs with an external portion having internal surface ribs. (FIG. 25-26). Introducer 114 may be configured to position and/or expand body 204. Introducer 114 may be configured to disengage and/or engage the interior and exterior portions. All or any portion of the length of introducer 114 may include one or more positioning members (not shown) having a hook, ratchet, tab, fastener, or ramp shape, for example, to disengage and/or engage the interior and exterior portions. Introducer 114 may have a graduated or tapered width along all or any portion of its length, for example, to provide controlled expansion of body 104/204.

In use, introducer 114 may be positioned in the passage body 204 a contracted condition (FIG. 25) with the positioning member between the overlapping interior and exterior portions of body 204. After body 204 is positioned, the positioning member of introducer 114 may urge or pull the interior portion inwards and/or urge or push the exterior portion outwards, for example by rotating introducer 114 and interior portion in a first direction relative to the exterior portion. While the internal and external portions are at least partially separated, the introducer 114 may be urged in an axial direction thereby advancing the graduated or tapered width relative to body 204 to increase expansion of body 204. After body 204 is expanded, the positioning member may be removed or rotated in an opposite, second direction to allow the interior and exterior portions to re-engage with body 204 in an expanded configuration. (FIG. 26).

Figure 27:
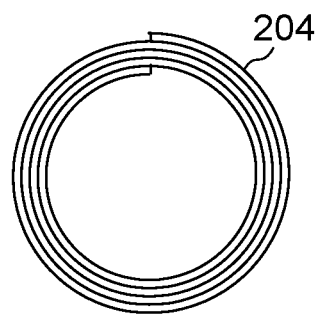
FIG. 27 illustrates an embodiment of the present disclosure, for example, including substantially aligned first and second ends.
Figure 28:
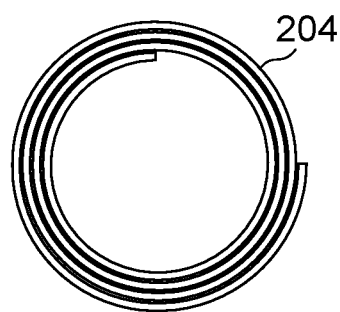
FIG. 28 illustrates an embodiment of the present disclosure, for example, including offset first and second ends.
Figure 29:
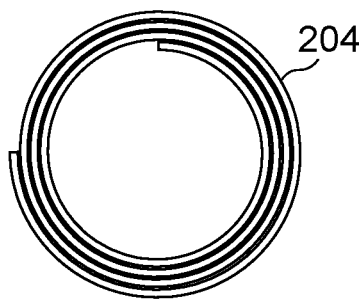
FIG. 29 illustrates an additional embodiment of the present disclosure, for example, including first and second ends in a reversed configuration.
Figure 30:
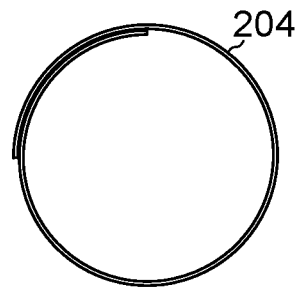
FIG. 30 illustrates an embodiment of the present disclosure, for example, first and second ends with about 25 percent overlap.
Figure 31:
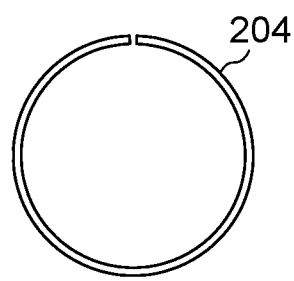
FIG. 31 illustrates an embodiment of the present disclosure, for example, first and second ends with a gap.
Figure 32:
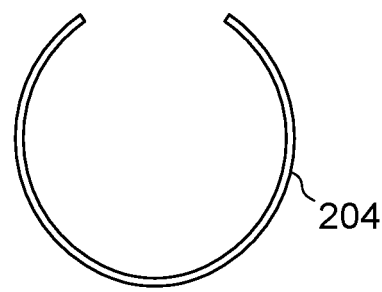
FIG. 32 illustrates the embodiment of FIG. 31, for example, in an expanded configuration.

All or any portion of a first end of body 204 may be overlapped by, aligned with, offset from, and/or have a gap with respect to all or any portion of a second end of body 204 in the contracted and/or expanded configurations. (FIGS. 27-32). Body 204 may overlap itself anywhere from around 1 to 100% or more, preferably about 20-50% overlap in the expanded condition. (FIGS. 27-29). Body 204 may be wrapped around itself more times in the contracted configuration than in the expanded configuration, for example, due to unraveling of body 204 between the contracted and expanded configurations. Alternatively, body 204 may have a gap in the non-expanded and/or expanded configurations. (FIGS. 31-32). Body 204 may also be wrapped in either direction. (FIGS. 28-29).

Embodiments may include dimensions of any magnitude. As operative example ranges, body 204 may be overlapped about 1 to 7 times in a contracted configuration ("contracted overlaps") and/or have a contracted inner diameter ("CID")

of about 2 to 3 mm, an expanded inner diameter ("EID") of about 4-17 mm, a contracted outer diameter ("COD") of about 2 to 5 mm contracted, and/or an expanded outer diameter ("EOD") of about 4 to 17 mm. As a first example, body 204 may have about 1 to 2 contracted overlaps (i.e. about 1.6), CID of about 2 to 3 mm (i.e. about 2.4 mm), EID of about 3 to 5 mm (i.e. about 4 mm), COD of about 2 to 4 mm (i.e. about 2.8 mm), and/or EOD of about 3 to 5 mm (i.e. about 4.3 mm). As a second example, body 204 may have about 2 to 3 contracted overlaps (i.e. about 2.4), CID of about 2 to 3 mm (i.e. about 2.4 mm), EID of about 5 to 7 mm (i.e. about 6 mm), COD of about 2 to 4 mm (i.e. about 3 mm), and/or EOD of about 5 to 7 mm (i.e. about 6.3 mm). As a third example, body 204 may have about 2 to 4 contracted overlaps (i.e. about 3.2), CID of about 2 to 3 mm (i.e. about 2.4 mm), EID of about 7 to 9 mm (i.e. about 8 mm), COD of about 2 to 4 mm (i.e. 3.2 mm), and/or EOD of about 7 to 9 mm (i.e. 8.3 mm). As a fourth example, body 204 may have about 3 to 5 contracted overlaps (i.e. 4), CID of about 2 to 3 mm (i.e. about 2.4 mm), EID of about 9 to 11 mm (i.e. about 10 mm), COD of about 2 to 4 mm (i.e. about 3.4 mm), and/or EOD of about 9 to 11 mm (i.e. about 10.3 mm). As a fifth example, body 204 may have about 4 to 6 contracted overlaps (i.e. 4.8), CID of about 2 to 3 mm (i.e. about 2.4 mm), EID of about 11 to 13 mm (i.e. about 12 mm), COD of about 2 to 5 mm (i.e. about 3.6 mm), and/or EOD of about 9 to 11 mm (i.e. about 12.3 mm). As a sixth example, body 204 may have about 5 to 6 contracted overlaps (i.e. 5.6), CID of about 2 to 3 mm (i.e. about 2.4 mm), EID of about 11 to 13 mm (i.e. about 14 mm), COD of about 3 to 5 mm (i.e. about 3.8 mm), and/or EOD of about 9 to 11 mm (i.e. about 14.3 mm). As a seventh example, body 204 may have about 6 to 7 contracted overlaps (i.e. about 6.4), CID of about 2 to 3 mm (i.e. about 2.4 mm), EID of about 11 to 13 mm (i.e. about 16 mm), COD of about 3 to 5 mm (i.e. about 4 mm), and/or EOD of about 9 to 11 mm (i.e. about 16.3 mm).

Figure 33:
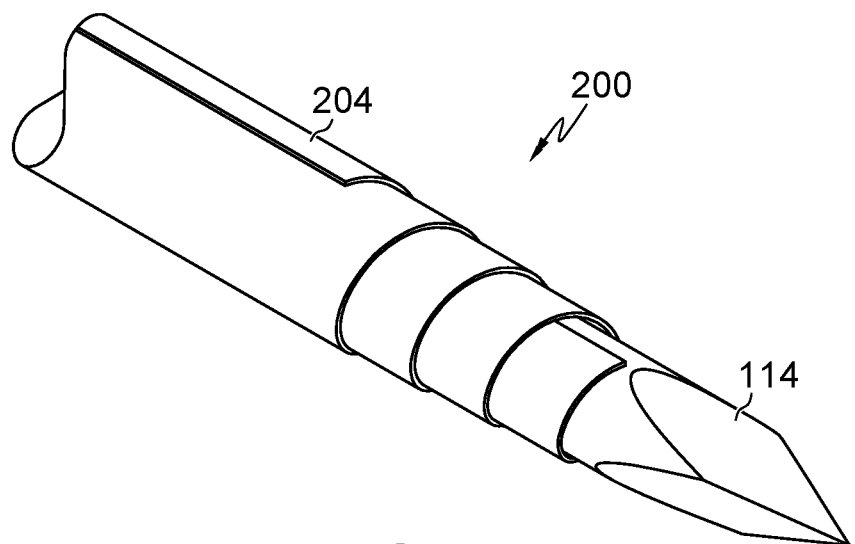
FIG. 33 illustrates an embodiment of the present disclosure, for example, including a pointed introducer and/or an offset wrapped configuration.
Figure 34:
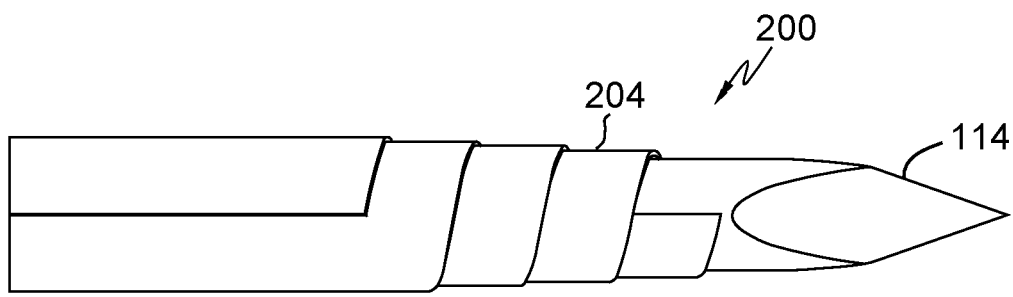
FIG. 34 illustrates a side view of the embodiment of FIG. 33.
Figure 35:
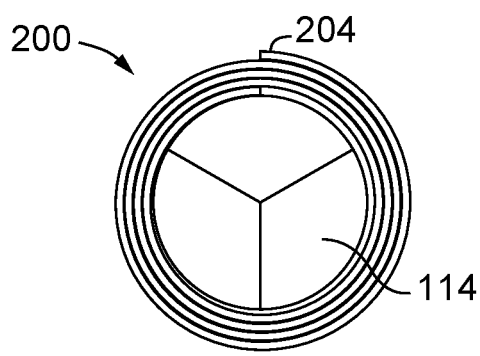
FIG. 35 illustrates a leading end view of the embodiment of FIG. 35.
Figure 36:
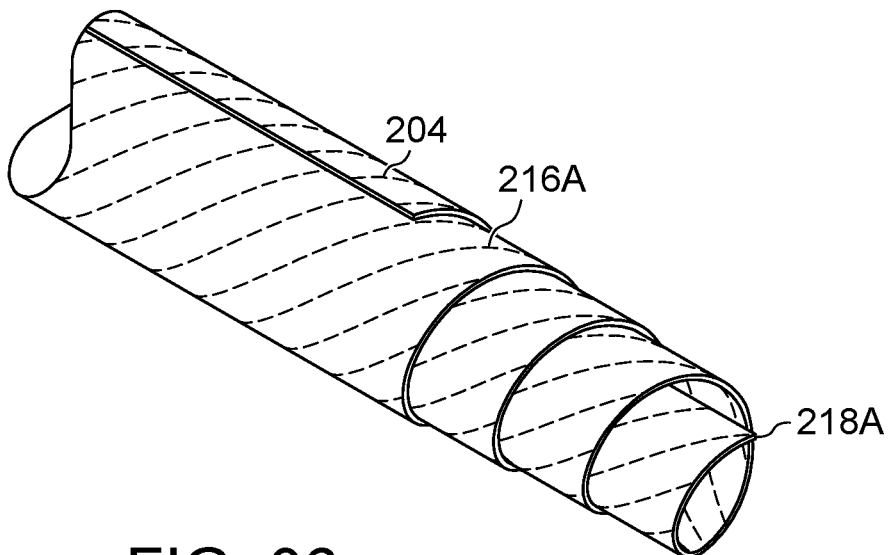
FIG. 36 illustrates an embodiment of the present disclosure, for example, including filaments and/or a pointed leading end.
Figure 41:
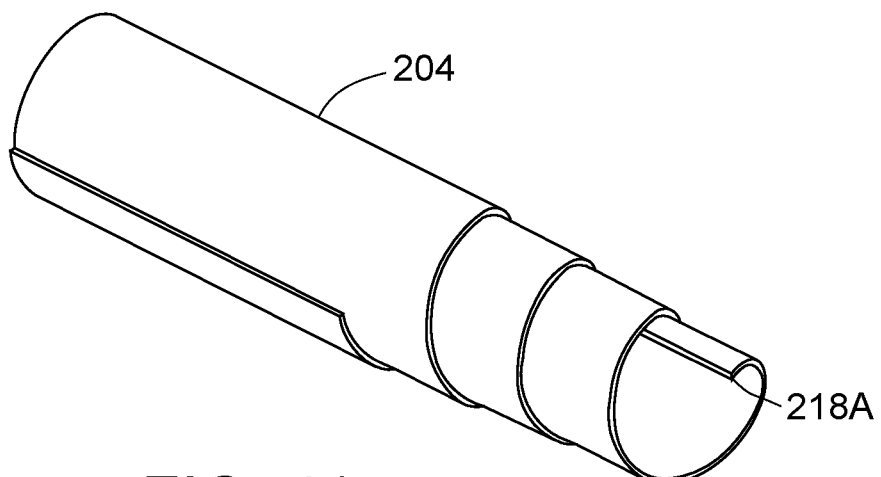
FIG. 41 illustrates an additional embodiment of FIGS. 36 and 37, for example, including a reversed configuration.
Figure 42:
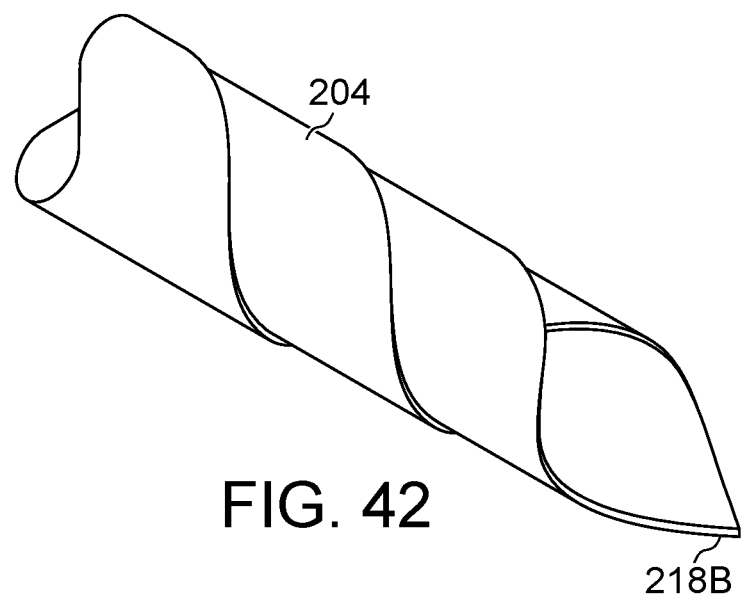
FIG. 42 illustrates an additional embodiment of the present disclosure, for example, including a pointed leading end.
Figure 43:
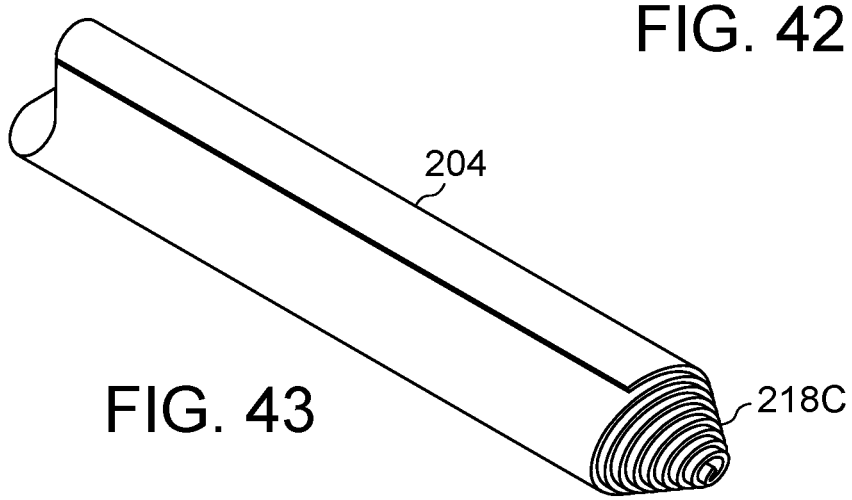
FIG. 43 illustrates an additional embodiment of the present disclosure, for example, including a pointed leading end.

Introducer 114 and/or body 104/204 may be configured to facilitate introduction into and/or piercing a tissue of the body of the patient. (FIGS. 33-43). A leading end of body 104/204 may include a sharp or pointed leading end and/or a sharp or pointed introducer 114. (FIGS. 33-35). Body 204 may be wrapped to form an offset, tapered, and/or angled orientation. (FIGS. 33-43). Body 204 may be configured to directly pierce a tissue of the body of the patient. Leading end 218A may be formed by wrapping body 204 at an angle. (FIG. 36). Alternatively, body 204 may be wrapped in the opposite direction. (FIG. 41). Leading end 218B may be formed by wrapping body 204 at a more aggressive angle (i.e. 45 degrees with respect to the first or second end) and/or performing an additional manufacturing operation to sharpen a tip of leading end 218B. (FIG. 42) Leading end 218C may be formed wrapping body 204 along the first or second end and then providing a force in the axial direction to urge a center portion into a taper. (FIG. 43)

Figure 37:
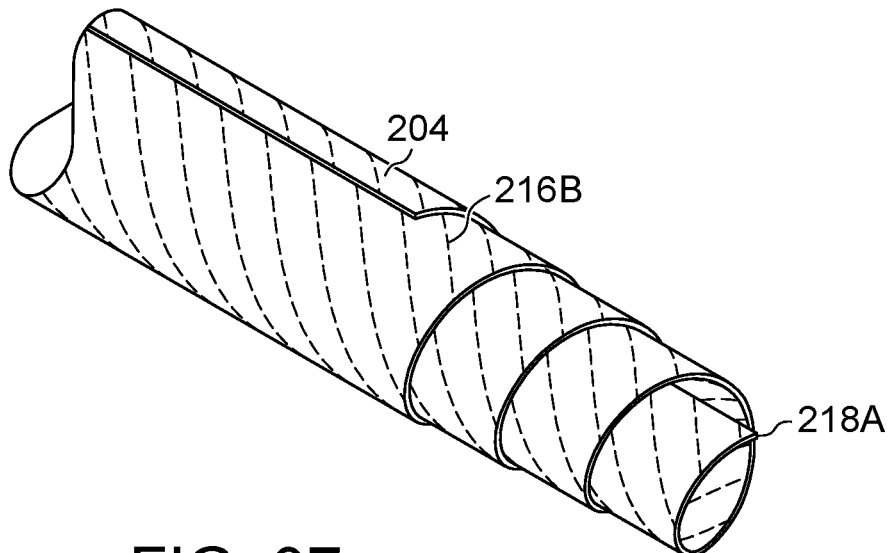
FIG. 37 illustrates an additional configuration of the embodiment of FIG. 36, for example, including opposing filaments.
Figure 38:
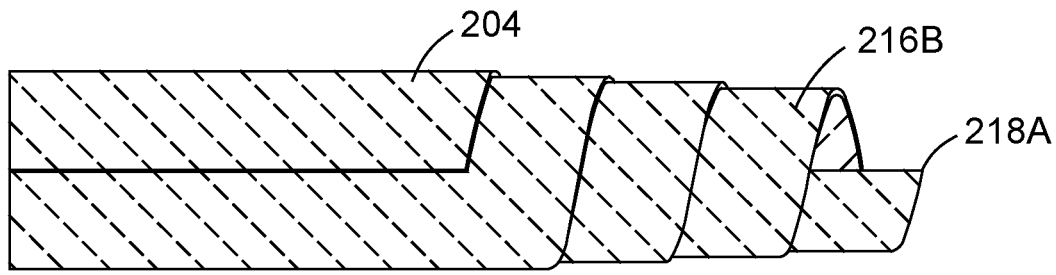
FIG. 38 illustrates a side view of the embodiment of FIG. 37.
Figure 39:
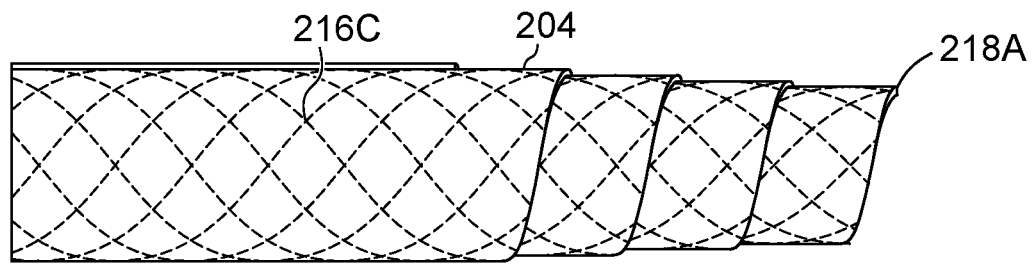
FIG. 39 illustrates an additional embodiment of FIGS. 36 and 37, for example, including a double helix configuration.
Figure 40:
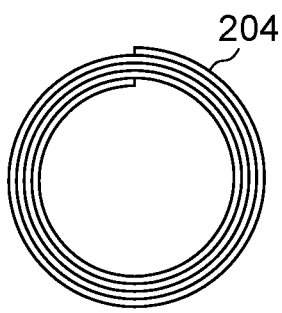
FIG. 40 illustrates a leading end view of the embodiment of FIG. 39.

Body 104/204 may include one or more filaments 216. (FIGS. 36-40). Body 104/204 may be made partially or entirely of a plurality of filaments 216. All or any portion of filaments 216 may be within body 204. Filaments 216 may be any material disclosed herein. For example, filaments 216 may be made of a metal material and/ort coated with a polymer material. Filaments 216A may be in a first direction, for example substantially following a wrap direction of body 204. (FIG. 36). Alternatively, filaments 216B may be in a second direction, for example substantially opposing the wrap direction of body 204. (FIG. 37-38). Filaments 216C may be in both the first and section directions, for example having a double helix configuration.

Figure 44:
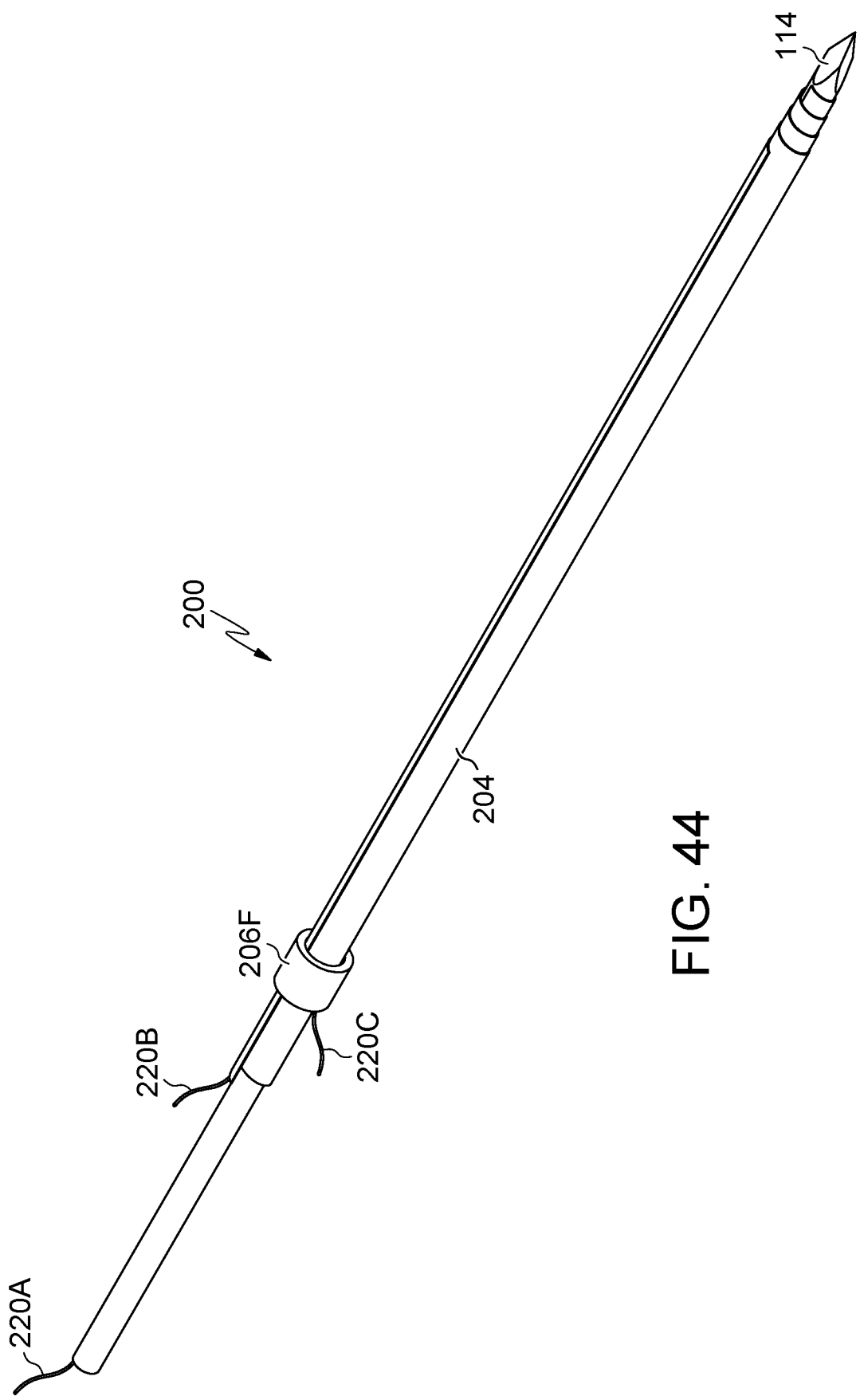
FIG. 44 illustrates an embodiment of the present disclosure, for example, including a band and/or wires.
Figure 47:
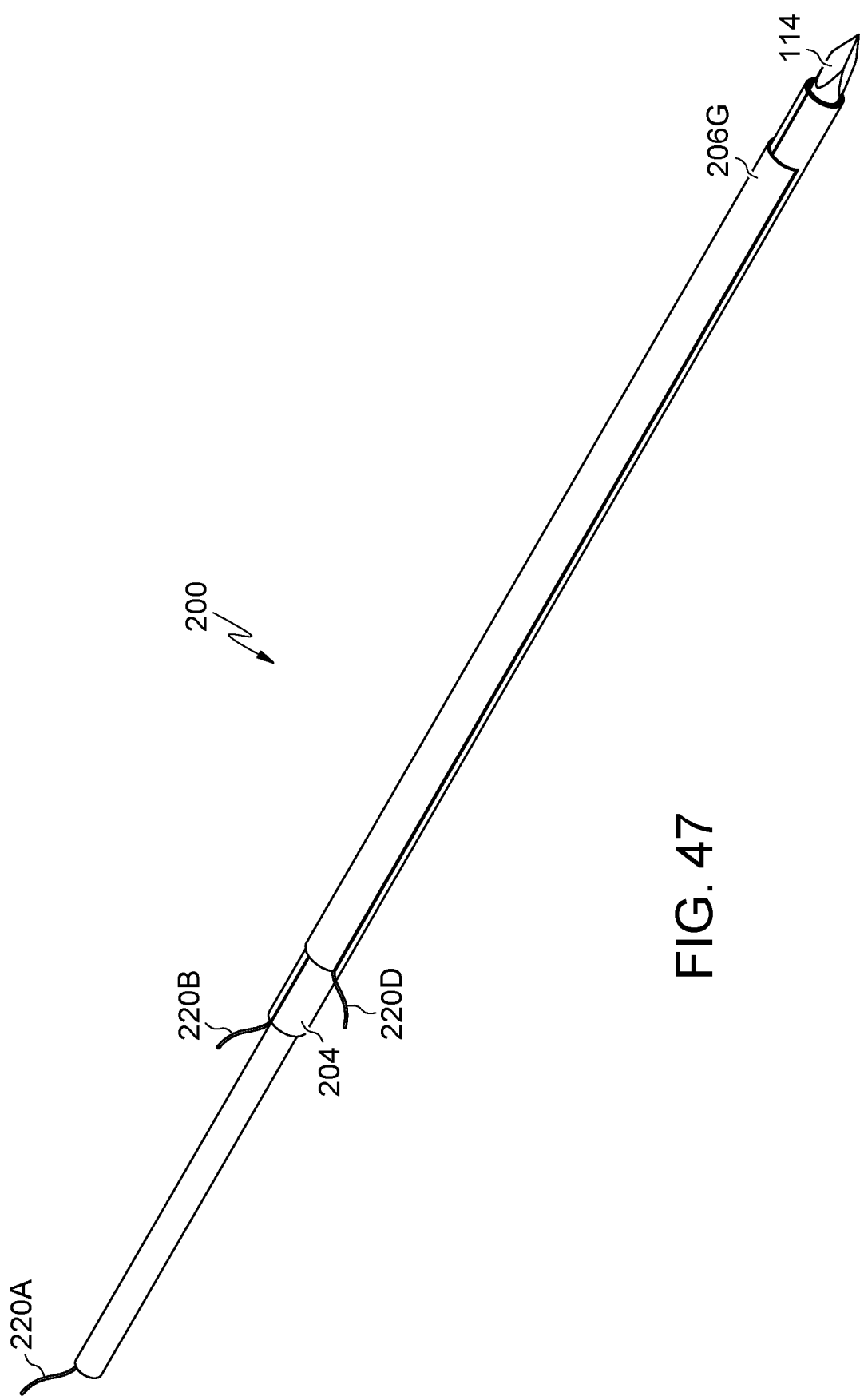
FIG. 47 illustrates an additional embodiment of the present disclosure, for example, including a band and/or wires.
Figure 48:
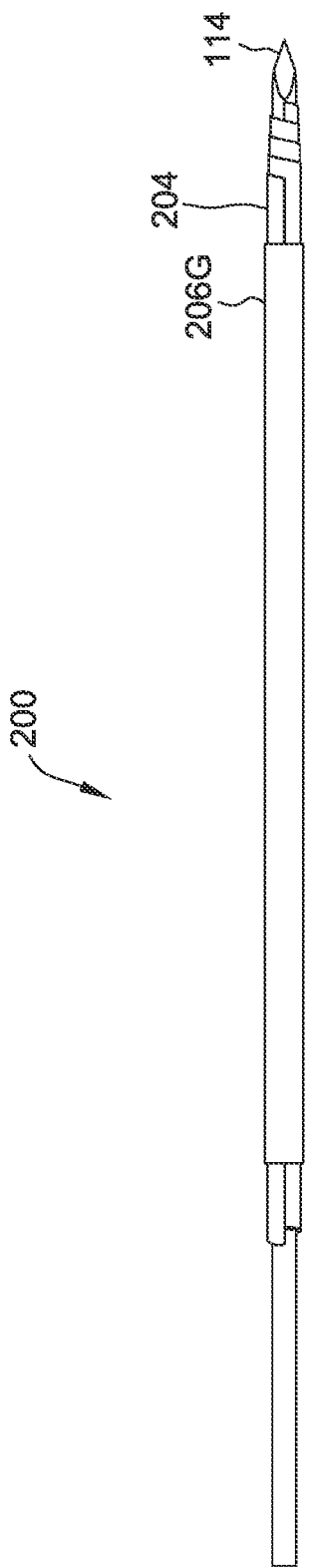
FIG. 48 illustrates a side view of the embodiment of FIG. 47.
Figure 49:
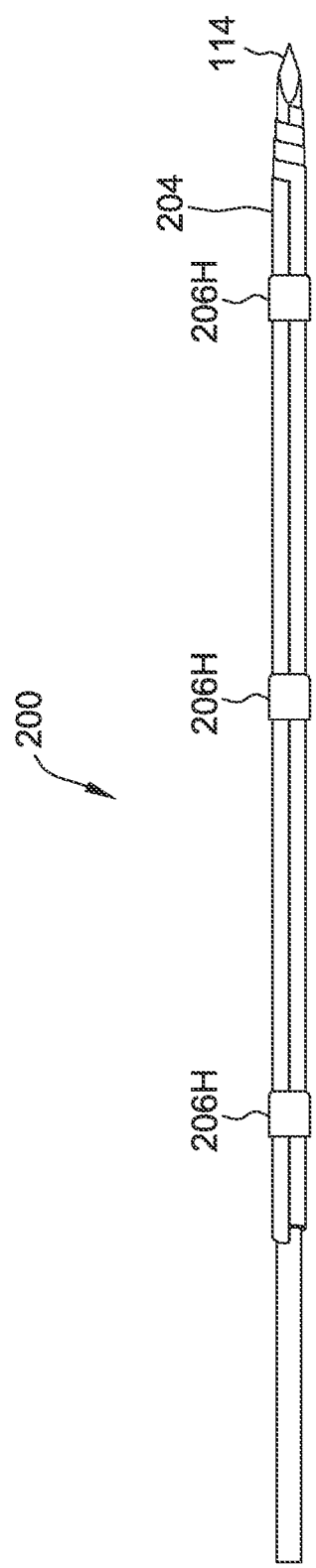
FIG. 49 illustrates an additional embodiment of FIGS. 44 and 47, for example, including multiple bands.
Figure 50:
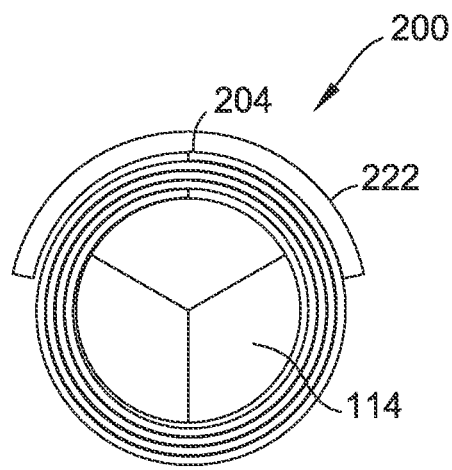
FIG. 50 illustrates a leading end view of the embodiment of FIG. 47.
Figure 51:
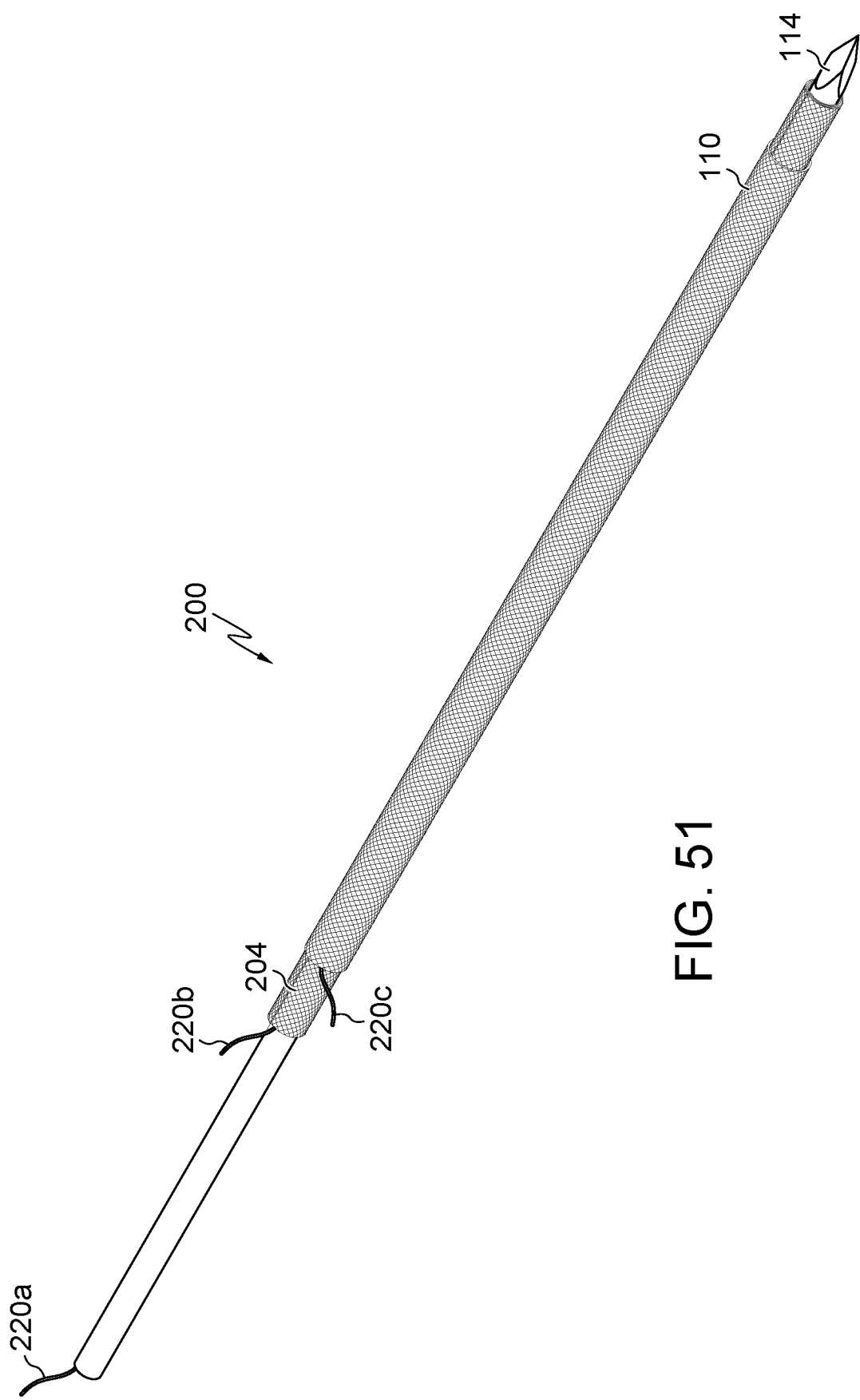
FIG. 51 illustrates an additional embodiment of FIGS. 44, 47, and 49, for example, including a mesh.

Embodiments may include wire 220, band 106/206, and/or a mesh. (FIGS. 44-51). Band 206F may radially constrain or adhere to all or a portion of the length body 104/205. (FIG. 44-46). Band 206G may radially constrain or adhere to all or a portion of the circumference of body 104/204. (FIGS. 47-48 and 50). Band 206H radially constrain or adhere to one or more locations across the length of body 104/204. (FIG. 49). Wire 220 may be connected to any or all of body 104/204, band 106/206, sleeve 110, and/or introducer 114. Body 104/204, band 106/206 (not shown), and/or sleeve 110 may include a mesh, filaments, and/or be expandable. (FIG. 51). Wire 220 may be configured to retract and/or remove any or all of body 104/204, band 106/206, sleeve 110, and/or introducer 114. Band 106/206 and/or sleeve 110 may be configured to urge and/or secure body 106/204 toward a substantially contracted configuration.

Figure 52:
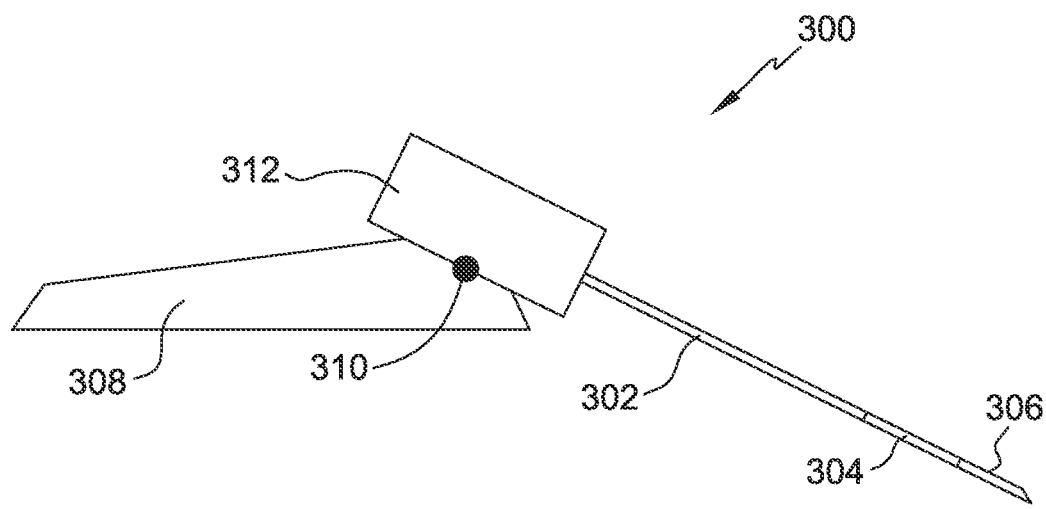
FIG. 52 illustrates an additional embodiment of the present disclosure, for example, including a base, connection, and support.
Figure 53:
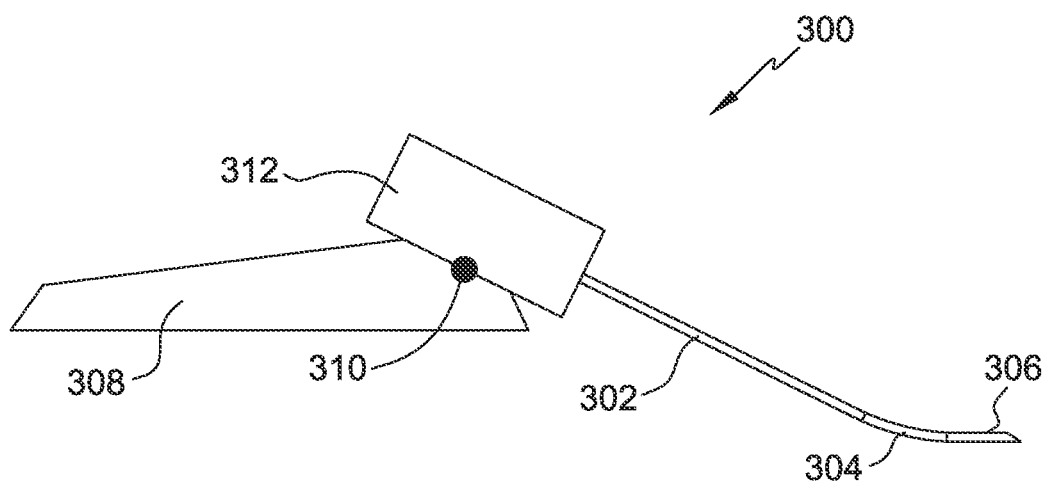
FIG. 53 illustrates the embodiment of FIG. 52, for example, including a curved configuration.

Systems 300/400 may be used and/or combined with system 100/200. System 300 may include elongate portion 302, middle portion 304, leading portion 306, base 308, connection 310, and support 312. (FIGS. 52-57). Elongate portion 302, middle portion 304, and/or leading portion 306 may be curved and/or bendable, for example, between an initial configuration (FIG. 52) and a substantially curved configuration (FIG. 53). Elongate portion 302, middle portion 304, and/or leading portion 306 may form body 104/204, trocar 112, introducer 114 or any cannula, guide wire, or any elongate structure configured to access a body portion or provide suction and/or injection of fluids with respect to the body of the patient. (FIG. 52-53). Connection 310 may connect base 308 and support 312, for example, to allow rotation and/or translation of support 312 relative to base 308. (FIG. 52) Connection 310 may include a pivot or a slide. Connection 310 may facilitate positioning of support 312 relative to an external or internal body portion or the desired access area.

Figure 54:
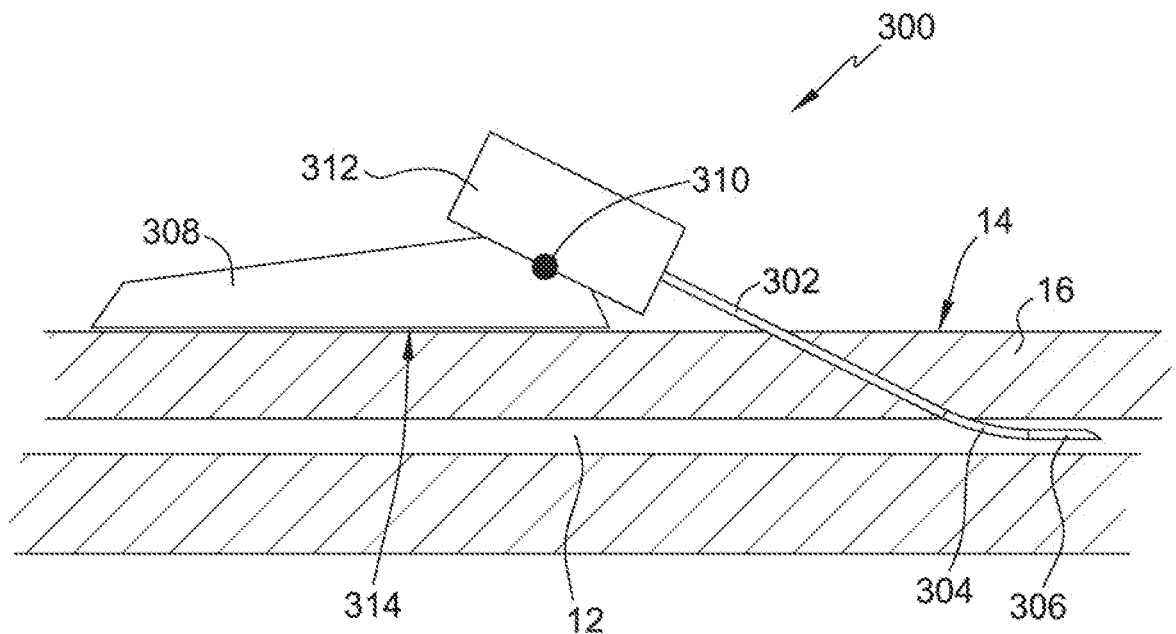
FIG. 54 illustrates an embodiment of the present disclosure, for example, including a body passage.
Figure 55:
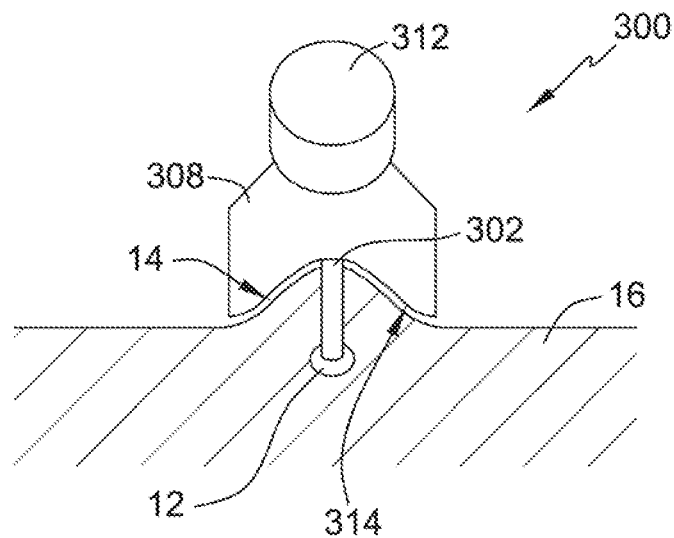
FIG. 55 illustrates a proximal end view of FIG. 54, for example, including a base shaped to a body tissue.
Figure 56:
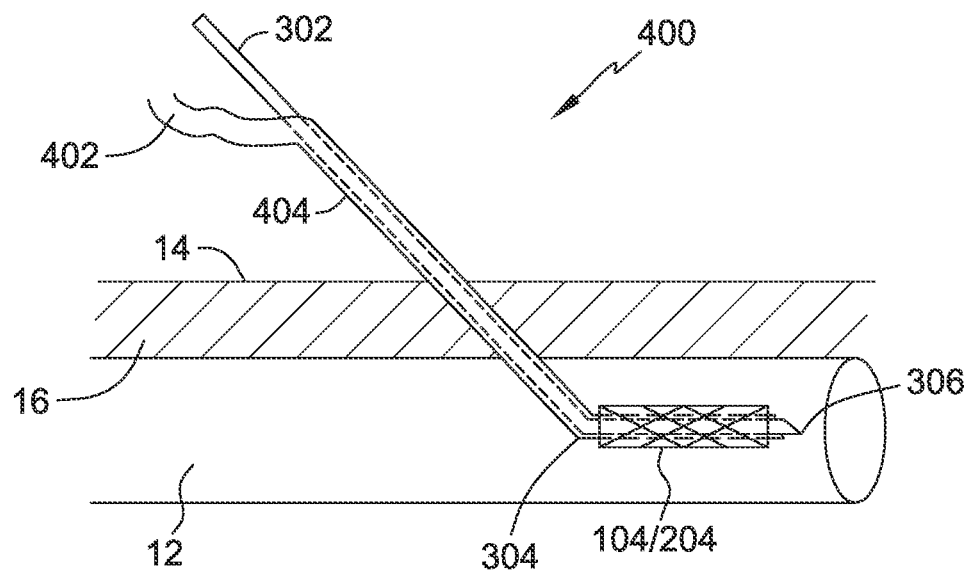
FIG. 56 illustrates an embodiment of the present disclosure, for example, including a pressure line and/or positioning an expandable device.

Base 308 may be configured to contact and/or approximate the anatomic surface features of body tissue 14 (FIG. 54-55). Base 308 may define the angle and/or position of support 312 with respect to body tissue 14, for example the external tissue (i.e. skin) adjacent to an internal passage (i.e. blood vessel). (FIG. 54-55). Connection 310 may connect base 308 and support 312, for example, to allow rotation and/or translation of support 312 relative to base 308. Connection 310 may include a pivot or a slide. Support 312 may include a handle and/or may be detachable from elongate portion 302 and/or base 308. Connection 310 may facilitate positioning of support 312 with respect to an external body portion, internal body portion, and/or access area.

In use, system 300/400 may be positioned adjacent an external body tissue with base 308 positioned on an external body portion. Connection 310 may allow support 312 to be positioned along a rotational and/or translational path that substantially aligns leading portion 306 with body passage 12. (FIGS. 54-55). Middle portion 304 may be positioned at a bend advantageous to access body passage 12 and/or may bend during penetration of body tissues 14 and/or 16. (FIG. 54). Support 312 may be urged toward body passage 12 thereby causing leading portion 306 to pierce the body tissues 14 and 16 and move into body passage 12. Elongate portion 302, middle portion 304, and leading portion 306 may also be detachable from support 312 and/or be used as a guide wire to position body 104/204 (i.e. a cannula or stent), trocar 112, pressure line 402, or another object.

System 400 additionally includes fluid connection 402, line 404, and body 104/204. System 400 may be positioned as discussed for system 300 with body 104/204 (i.e. stent) being positioned near leading portion 306. Fluid connection 402 may be coupled to a fluid or pressure source. Fluid connection 402 and/or line 404 may be configured to control expansion of body 104/204 with fluid pressure and/or provide suction and/or injection of fluids to body passage 12. Embodiments of the present disclosure may include any additional devices and methods disclosed in U.S. patent application Ser. No. 12/707,945, entitled "Anatomic Needle System", which is incorporated herein by reference in its entirety.

Embodiments may include an imaging device, for example providing indirect visualization. An imaging device may be used to identify and/or change the orientation or position of embodiments herein. Examples of indirect visualization may include endoscopic guidance, computer assisted navigation, magnetic resonance imaging (MM), CT scan, ultrasound, fluoroscopy, X-ray, or other visualization technique disclosed in any of the references incorporated herein. Asymmetric coating, radiopaque markers, or other features identifiable with indirect visualization may be used to identify and/or adjust orientation or position. Indirect visualization may also be used to align portions of a first device relative to a portion of the first device, a second device, or a body portion of a patient.

Embodiments may include a magnet, electromagnet, and/or magnetizable materials, which may emit a magnetic field. The electromagnet may selectively provide a magnetic field with application of current. The magnet, electromagnet, and/or magnetizable materials may be mounted on or included in all or any portion of the embodiments herein. For example, a leading end portion of body 104/204, trocar 112, and/or introducer 114 may be utilized to position the system. The magnetic field may emanate from a portion of the system or from an external source positioned outside the body. Magnetizable materials include ferrite particles, which may or may not be magnetized. The polarity and/or strength of the magnetic field may be increased, decreased, or alternated to controllably guide the system. Embodiments of the present disclosure may also include any devices and methods disclosed in U.S. Pat. No. 7,320,319, entitled "Medicant Delivery System and Method", U.S. patent application Ser. No. 12/134,083, entitled "Magnetic Joint Implant", and U.S. Pat. No. 6,719,765, entitled "Magnetic Suturing System and Method", all of which are incorporated herein by reference in their entirety.

In addition, embodiments of the present disclosure may include all or any portion of the embodiments disclosed in U.S. Pat. No. 6,814,715, entitled "Expandable Cannula"; U.S. Pat. No. 7,837,736, entitled "Minimally Invasive Surgical Systems and Methods"; U.S. patent application Ser. No. 11/549,994, entitled "Drug Eluting Implant"; U.S. patent application Ser. No. 11/867,679, entitled "Methods and Devices for Controlling Biologic Microenvironments"; U.S. patent application Ser. No. 13/559,352, entitled "Methods and Systems for Controlling Medical Environments"; U.S. patent application Ser. No. 11/842,648, entitled "Method of Inhibiting the Formation of Adhesions and Scar Tissue and Reducing Blood Loss", and U.S. patent application Ser. No. 10/945,331, entitled "Minimally Invasive Therapeutic System", all of which are incorporated herein by reference in their entirety.

As used herein, an element or act recited in the singular and proceeded with the word "a" or "an" should be understood as not excluding plural elements or acts unless such exclusion is explicitly recited. This written description uses examples to disclose various embodiments, which include the best mode, to enable any person skilled in the art to practice those embodiments, including making and using any devices or systems and performing any incorporated methods. Any materials disclosed herein may be used for any of the embodiments herein. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An expandable access system comprising:
a needle end trocar having a sharp leading end;
a cannula defining an access passage, the cannula configured to be positioned a contracted configuration around the needle end trocar;
a retaining component configured to resist radial expansion of the cannula,
wherein the needle end trocar is configured to directly penetrate through skin and into a body part,
wherein the needle end trocar is configured to be detached from the cannula and removed from the body part and the skin, and
wherein the cannula is configured to expand radially into an expanded configuration against the skin and body part to distract tissues when at least a portion of the retaining component is removed, such that the access passage created by the cannula in the expanded configuration is larger than the access passage defined by the cannula in the contracted configuration.

2. The system of claim 1, wherein the cannula and the needle end trocar are configured to mechanically interlock when the needle end trocar is configured to penetrate through skin and into a body part and configured to unlock when the needle end trocar is detached and removed, and the cannula is expanded.

3. The system of claim 1, wherein the access passage enables the removal of at least one of blood and body fluids from the body part.

4. The system of claim 1, further comprising features on the external surfaces of the cannula configured to engage with at least one of the body part and the tissues.

5. The system of claim 1, wherein the access passage enables the introduction of therapeutic substances to the body part, wherein the therapeutic substances are at least one of antibiotics, hydroxyapatite, anti-inflammatory agents, steroids, antibiotics, analgesic agents, chemotherapeutic agents, bone morphogenetic protein (BMP), demineralized bone matrix, collagen, growth promoting materials, growth factors, autogenetic bone marrow, progenitor cells, calcium sulfate, immunosuppressants, fibrin, osteoinductive materials, apatite compositions, germicides, fetal cells, adult cells, stem cells, enzymes, proteins, hormones, cell therapy substances, gene therapy substances, and combinations thereof.

6. The system of claim 1, wherein heating the cannula with an external energy source causes the cannula to at least one of expand into the expanded configuration and contract into the contracted configuration.

7. The system of claim 1, wherein cooling the cannula with an external energy source causes the cannula to at least one of expand into the expanded configuration and contract into the contracted configuration.

8. The system of claim 1, wherein the cannula in the expanded configuration has a variable cross-section along the length of the access passage.

9. The system of claim 1, wherein the access passage of the cannula in the expanded configuration is configured to connect to a fluid connection including a fluid line, wherein the fluid connection is coupled to at least one of a fluid source and a pressure source.

10. The system of claim 1, wherein the access passage enables the introduction of at least one implant to the body part.

11. The system of claim 1, wherein the body part is at least one of a vessel and a lumen.

12. An expandable access system comprising:
a needle end trocar having a sharp leading end;
a cannula defining an access passage, the cannula configured to be positioned in a contracted configuration around the needle end trocar;
a retaining component configured to resist radial expansion of the cannula,
wherein the needle end trocar is configured to directly penetrate through skin and into a vascular structure,
wherein the needle end trocar is configured to be detached from the cannula and removed from the vascular structure and the skin, and
wherein the cannula is configured to expand radially into an expanded configuration against the skin and vascular structure to distract tissues when at least a portion of the retaining component is removed, such that the access passage created by the cannula in the expanded configuration is larger than the access passage defined by the cannula in the contracted configuration.

13. The system of claim 12, wherein the vascular structure is at least one of a vessel, vein, artery, and heart.

14. The system of claim 12, wherein the access passage enables the removal of at least one of blood and body fluids from the body part.

15. The system of claim 12, wherein the access passage enables the introduction of therapeutic substances to the vascular structure, wherein the therapeutic substances are at least one of antibiotics, hydroxyapatite, anti-inflammatory agents, steroids, antibiotics, analgesic agents, chemotherapeutic agents, bone morphogenetic protein (BMP), demineralized bone matrix, collagen, growth promoting materials, growth factors, autogenetic bone marrow, progenitor cells, calcium sulfate, immunosuppressants, fibrin, osteoinductive materials, apatite compositions, germicides, fetal cells, adult cells, stem cells, enzymes, proteins, hormones, cell therapy substances, gene therapy substances, and combinations thereof.

16. The system of claim 12, wherein heating the cannula with an external energy source causes the cannula to at least one of expand into the expanded configuration and contract into the contracted configuration.

17. The system of claim 12, wherein cooling the cannula with an external energy source causes the cannula to at least one of expand into the expanded configuration and contract into the contracted configuration.

18. The system of claim 12, wherein the cannula in the expanded configuration has a variable cross-section along the length of the access passage.

19. The system of claim 12, wherein the access passage of the cannula in the expanded configuration is configured to connect to a fluid connection including a fluid line, wherein the fluid connection is coupled to at least one of a fluid source and a pressure source.

20. The system of claim 12, wherein the access passage enables the introduction of at least one implant into the vascular structure configured to remain in the vascular structure after removal of the cannula, wherein the at least one implant is at least one of a stent, a cardiac implant, and a vascular implant.

* * * * *